(12) United States Patent
Damren et al.

(10) Patent No.: US 11,130,073 B2
(45) Date of Patent: *Sep. 28, 2021

(54) SYSTEM AND METHOD FOR CONDENSING MOISTURE IN A BIOREACTOR GAS STREAM

(71) Applicant: Global Life Sciences Solutions USA LLC, Marlborough, MA (US)

(72) Inventors: Richard Lee Damren, Marlborough, MA (US); Colin Tuohey, Marlborough, MA (US); Patrick Guertin, Mendon, MA (US); Parrish Galliher, Marlborough, MA (US)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/752,932

(22) Filed: Jan. 27, 2020

(65) Prior Publication Data

US 2020/0155962 A1 May 21, 2020

Related U.S. Application Data

(63) Continuation of application No. 14/974,833, filed on Dec. 18, 2015, now Pat. No. 10,576,393.

(51) Int. Cl.
*B01D 5/00* (2006.01)
*C12M 1/00* (2006.01)
(Continued)

(52) U.S. Cl.
CPC ......... *B01D 5/0042* (2013.01); *B01D 5/0027* (2013.01); *B01D 5/0051* (2013.01);
(Continued)

(58) Field of Classification Search
None
See application file for complete search history.

(56) References Cited

U.S. PATENT DOCUMENTS

| | | |
|---|---|---|
| D135,633 S | 5/1943 | Stark et al. |
| 4,423,766 A | 1/1984 | Bernhardt et al. |
| | (Continued) | |

FOREIGN PATENT DOCUMENTS

| | | |
|---|---|---|
| CN | 1903908 A | 1/2007 |
| DE | 10 2005 012732 | 9/2006 |
| DE | 10 2011 007543 | 10/2012 |

*Primary Examiner* — T. Bennett McKenzie
*Assistant Examiner* — Phillip Y Shao
(74) *Attorney, Agent, or Firm* — Grogan, Tuccillo & Vanderleeden, LLP

(57) ABSTRACT

Disclosed herein is a system and method for condensing moisture in a gas stream entering or leaving a bioreactor, the system comprising: a contact condenser container fluidically coupled to the bioreactor through an exhaust line; a condensate accumulator fluidically coupled to the contact condenser container through at least a first condensate line and a second condensate line; the condensate accumulator further fluidically coupled to the bioreactor through a condensate overflow line; a first condensate control device disposed on the first condensate line and configured to control a flow of condensate leaving the contact condenser container and entering the condensate accumulator; and a second condensate control device disposed on the second condensate line and configured to control a flow of condensate leaving the condensate accumulator to be mixed with the gas stream.

20 Claims, 20 Drawing Sheets

(51) Int. Cl.
   *B01D 53/84* (2006.01)
   *B01D 53/26* (2006.01)

(52) U.S. Cl.
   CPC ........... *B01D 53/265* (2013.01); *B01D 53/84* (2013.01); *C12M 29/26* (2013.01)

(56) References Cited

U.S. PATENT DOCUMENTS

| | | |
|---|---|---|
| 5,466,776 A | 11/1995 | Krautstrunk et al. |
| 2003/0035752 A1 | 2/2003 | Askenov et al. |
| 2010/0162619 A1 | 7/2010 | Peus |
| 2010/0170400 A1 | 7/2010 | van den Boogard et al. |
| 2010/0261242 A1 | 10/2010 | Harvey et al. |

SYSTEM AND METHOD FOR CONDENSING MOISTURE IN A BIOREACTOR GAS STREAM

APPLICATION CROSS-REFERENCE

This Application is a continuation of application Ser. No. 14/974,833 filed 18 Dec. 2015 the entirety of which is hereby incorporated by reference.

TECHNICAL FIELD

The present invention relates generally to systems and methods for use with disposable bioreactors or with non-disposable tank bioreactors.

BACKGROUND

Cell culturing is an essential step in manufacturing biological products, and may be carried out in disposable bioreactors or in non-disposable bioreactors such as steel tank vessels. Oxygen is continuously supplied to promote cell growth, and carbon dioxide is removed. A gas stream entering or leaving a bioreactor may contain moisture entrained within the gas stream. The moisture in the moisture-containing gas stream may condense as the gas stream passes through a filter or other system components. The moisture and/or condensation may be detrimental to the functioning of the filter or other system components. Typically a condenser is used for condensing moisture in a moisture-containing gas stream entering or leaving a bioreactor.

A number of yet un-solved problems are inherent in currently available condenser designs for use with bioreactors. Some related art design incorporate several functionally different areas such as, for example, subducts and different cooling and heating zones, that result in a complex and costly assembly requiring special tooling, specially molded or machined components. Because related art designs are complex and tend to be expensive, such condensers are not truly disposable.

Currently available condensers may have another drawback in that the condensate that is generated from condensing moisture in a moisture-containing gas stream is wasted by being poured into the environment to get rid of it.

Yet another drawback of currently available condenser designs is related to the bioreactor reaction volume loss. If the water vapor from the bioreactor reaction mixture is lost over time and not replenished, then the osmolality of the bioreactor reaction mixture may change to an undesirable level.

Therefore, there is a need for an improved system, in particular, a truly disposable or single-use system and corresponding method that provide a means to reduce the moisture content of a moisture-containing gas stream within a bioreactor system before it passes to a filter or other system components, minimize wasting the condensate generated, and minimize the loss of the bioreactor reaction volume.

SUMMARY

The embodiments disclosed in the present invention for the system and associated method for condensing moisture in a bioreactor gas stream overcome many of the problems found in currently available condensers. However, the embodiments disclosed in the present invention should not be limited to solving only the problems stated in the applications, but may solve other problems in other areas.

The invention includes, but is not limited to, the following embodiments:

One embodiment includes a system for condensing moisture in a gas stream entering or leaving a bioreactor, the system comprising: a contact condenser container fluidically coupled to the bioreactor through an exhaust line; a condensate accumulator fluidically coupled to the contact condenser container through at least a first condensate line and a second condensate line; the condensate accumulator further fluidically coupled to the bioreactor through a condensate overflow line; a first condensate control device disposed on the first condensate line and configured to control a flow of condensate leaving the contact condenser container and entering the condensate accumulator; and a second condensate control device disposed on the second condensate line and configured to control a flow of condensate leaving the condensate accumulator to be mixed with the gas stream.

Another embodiment includes a method for condensing moisture in a gas stream entering or leaving a bioreactor, the method comprising: directing the gas stream leaving the bioreactor and entering the contact condenser container; producing a condensate inside the contact condenser container; directing and controlling a flow of the condensate leaving the contact condenser container and entering the condensate accumulator; and directing and controlling a flow of at least a portion of the condensate leaving the condensate accumulator to be mixed with the gas stream.

Yet another embodiment includes a system for condensing moisture in a gas stream entering or leaving a bioreactor, the system comprising: a contact condenser container fluidically coupled to the bioreactor through an exhaust line; a junction fitting fluidically coupled to the contact condenser container through a first and a second condensate line; the condensate accumulator further fluidically coupled to the bioreactor through a condensate overflow line; a first condensate control device disposed on the first condensate line and configured to control a flow of condensate leaving the contact condenser container into the junction fitting; and a second condensate control device disposed on a second condensate line and configured to control a flow of condensate leaving the condensate accumulator to be mixed with the gas stream, wherein the flow of condensate is used to provide cooling to the gas stream.

BRIEF DESCRIPTION OF THE DRAWINGS

The various advantages of the embodiments will be apparent to one skilled in the art by reading the following specification and appended claims, and by referencing the following drawings, in which:

DETAILED DESCRIPTION

Figure 1:
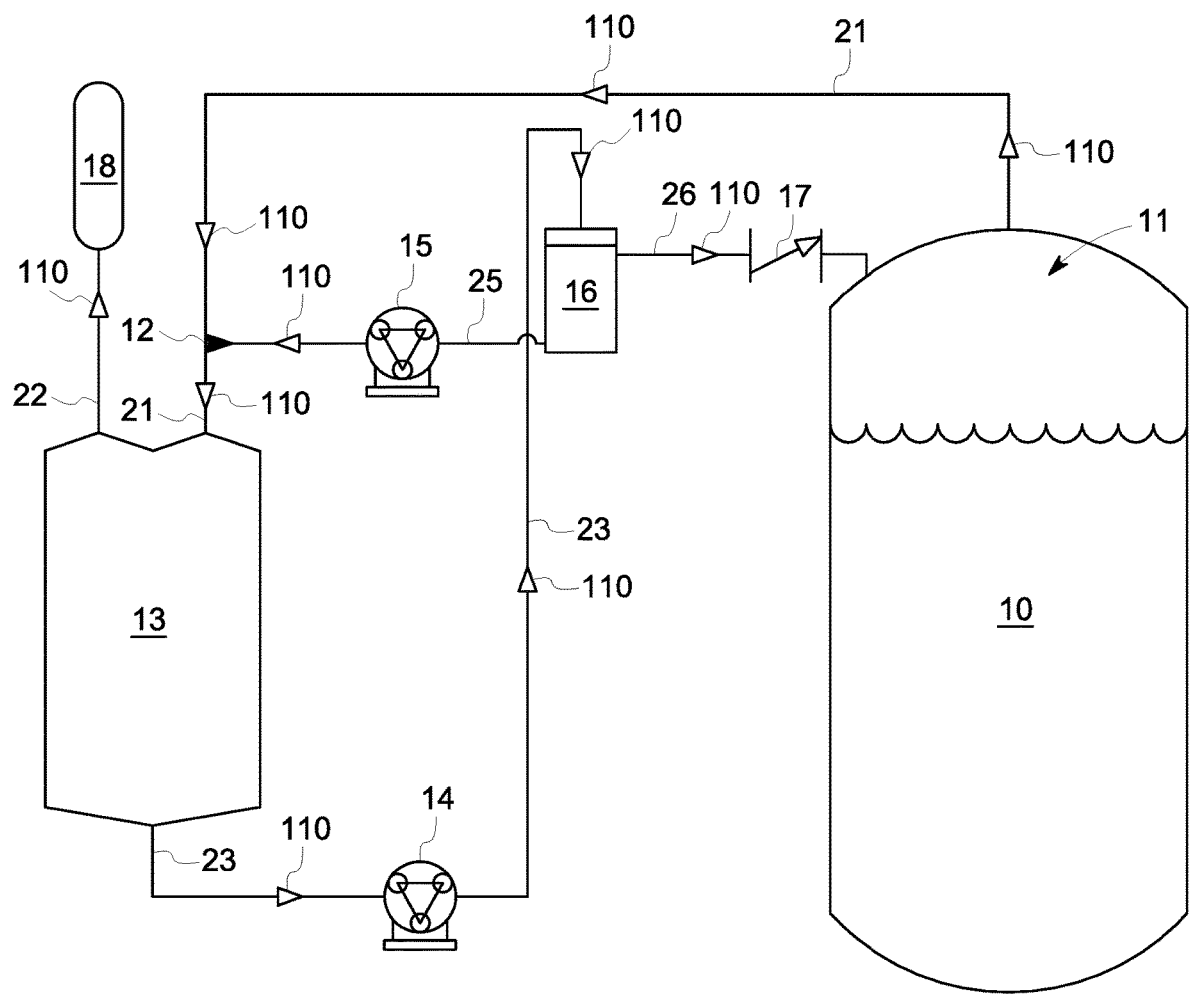
FIG. 1 is a schematic drawing of an example of a system according to an embodiment.

Any examples or illustrations given herein are not to be regarded in any way as restrictions on, limits to, or express definitions of, any term or terms with which they are utilized. Instead, these examples or illustrations are to be regarded as being described with respect to various particular embodiments and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to: "for example", "for instance", "such as", "e.g.", "including", and "in one (an) embodiment".

The term "bioreactor" as used herein generally refers to a device or apparatus in the form of a closed chamber or vessel in which living organisms such as mammalian cells, bacteria or yeast synthesize substances useful, for example, to the pharmaceutical industry under controlled conditions favorable to that specific organism. Traditionally bioreactors were closed, rigid stainless steel vessels in which the organisms were grown. The term "bioreactor" as used herein may be rigid or disposable, single-use bioreactor.

The term "disposable" or "single-use" as used herein in the context of a bioreactor generally refers to a flexible container, liner or bag incorporating all of the functional aspects required of a traditional bioreactor which can be filled with the materials required for the growth of mammalian cells, bacteria or yeast and is designed with the intention that it be disposed of at the completion of a single production run.

The term "moisture-containing gas stream" as used herein generally refers to a gas stream entering or leaving a bioreactor and contains moisture entrained within the moisture-containing gas stream. The moisture-containing gas stream may be referred to as a "gas stream" or a "moist gas stream".

The term "dry gas stream" as used herein generally refers to a gas stream with moisture entrained within the gas stream substantially removed.

The term "contact condenser container" as used herein generally refers to a condenser container in which a recycled condensate makes direct contact with a moisture-containing gas stream to assist in removing moisture from the gas stream.

For a discussion of the condenser container, see for example, U.S. 20120260671 A1 published on Oct. 18, 2012, which is incorporated herein by reference. The condenser container may be either a single use, flexible, nonporous bag comprising, for example, a flexible polyethylene material or film, or a rigid or a semi-rigid container instead of a flexible bag. The condenser container may be referred to as a "bag", a "condenser bag" or a "flexible bag".

The term "recycled condensate" as used herein generally refers to a relatively cool condensate that is initially generated from condensing moisture in a relatively hot moisture-containing gas stream entering or leaving a bioreactor and is reused or recycled by either having at least a portion of the relatively cool condensate introduced back into and mixed with the moisture-containing gas stream or having a portion of the cool condensate introduced back into a bioreactor. The recycled condensate may be referred to as a "condensate", a "cool condensate", or a "relatively cool condensate".

The term "condensate recycling process" as used herein generally refers to a process involving reusing or recycling of a relatively cool condensate generated from condensing moisture in a moisture-containing gas stream entering or leaving a bioreactor.

The term "condensate accumulator" as used herein generally refers to devices or apparatus used with bioreactors. The condensate accumulator is configured to hold or store the a relatively cool condensate collected from a condenser container prior to at least a portion of the condensate being introduced back into and mixed with a relatively hot moisture-containing gas stream. The condensate accumulator may be either rigid stainless steel vessels or disposable and/or single-use systems and are compatible with both disposable and non-disposable bioreactors.

The term "condensate flow control device" as used herein generally refers to devices or apparatus used to direct and/or control the flow of the condensate. The condensate flow control device may comprise a pump, a check valve, or a nozzle, a pressurized air source, or a combination thereof. The features of the condensate flow control device are described in more details in the detailed description section. The terms "condensate flow control system" and "condensate flow control device" may be used interchangeably.

The term "condensate overflow control device" as used herein generally refers to devices or apparatus used to direct and/or control the condensate overflow from the condensate accumulator to the bioreactor. The condensate overflow control device may comprise a pump, a check valve, a nozzle, or a pressurized air source, or a combination thereof.

The term "disposable" or "single-use" as used herein in the context of a contact condenser container, a condensate accumulator, a condensate flow control device, and a condensate overflow control device generally refers to a device designed to be low cost and to incorporate materials which can be easily disposed of using commonly available waste processing infrastructure and not requiring special disposal procedures. Non-limiting examples of materials which can be easily disposed of comprise polyethylene, polypropylene, polyester, or polyamide, or combination thereof. The materials may further comprise gamma-irradiation stable materials. Non-limiting examples of materials that are considered gamma-irradiation stable comprise polyethylene, polypropylene, polyester, polyamide, polysulfone, polycarbonate, polyvinylidene fluoride, or polyurethane, or combination thereof. The device may further comprise pre-sterilized components with sanitary connectors or tubings suitable for sterile welding.

The term "coupled" as used herein is intended to signify that distinct elements are joined, linked or otherwise connected together directly and/or indirectly.

The term "flow direction" as used herein is generally represented by a reference numeral 110. It is to be understood that 110 is not limited to one specific flow direction arrangement, rather, 110 may be used to represent various flow arrangements for a fluid flow.

In one embodiment, a relatively cool condensate is generated while a relatively hot moisture-containing gas stream passes through a condenser container. Instead of being sent to waste, the condensate generated is directed to a condensate accumulator and recycled by having at least a portion of the condensate transferred out of the condensate accumulator, introduced back into and mixed with the moisture-containing gas stream to provide further cooling and condensation of the moisture in the gas stream. Recycling condensate increases the overall efficiency of the moisture removal from the moisture-containing gas stream. The mixing of the recycled condensate with the moisture-containing gas stream may occur either in a location inside the exhaust line coupling the bioreactor to the contact condenser container or inside the contact condenser container itself.

The condensate recycling process may comprise three stages. The initial stage comprises a "priming stage" which occurs during the early phase of a bioreactor run when very little cool condensate is produced inside the condenser container. Therefore, there may not be sufficient condensate to introduce a continuous flow of recycled condensate back into the moisture-containing gas stream. Alternatively, the priming may be done manually by adding sterile filtered water to the condensate accumulator via a condensate priming system comprising a priming fitting and a sterile filter, which are described in detail in FIG. 21.

The second stage occurs when more recycled condensate is introduced back into the gas stream and facilitates more efficient moisture condensation. As a result a continuous flow of recycled condensate being introduced back into the gas stream may be established. This is a stage when the cooling efficiency of the contact condenser container becomes greater, and is considered to be a positive feedback stage.

As more and more condensate is produced the recycling process reaches a third stage where the condensate level inside the condensate accumulator increases to a condensate overflow mark and the overflow condensate is transferred to the bioreactor. Thus, negative impacts due to the bioreactor reaction volume loss may be minimized. At the third stage, there is a relatively constant flow of recycled condensate back into the gas stream since almost all of the recycled condensate introduced back into and/or mixed with the gas stream is quickly recovered from the contact condenser container and transferred to the condensate accumulator.

The condensate recycling process may be controlled or adjusted by a condensate flow control system. The condensate flow control system may be used in conjunction of a bioreactor control system including, but not limited to, various bioreactor sensors to provide further control of the condensate recycling process. Non-limiting examples of bioreactor sensors include sensors for pH, concentration, or osmolality, or combination thereof.

The condensate generated within the contact condenser container may be released or drained from the contact condenser container either continually or periodically. The condensate may be drained through an inlet port fitment. Alternatively, there may be a separate fitment, for example, a hose barb (not shown) attached to a surface of the contact condenser container specifically for draining the condensate. The hose barb may be used for attaching and securing a tubing to collect the condensate.

The condensate leaving the condensate accumulator may be introduced back into and mixed with the gas stream in a form of a spray of condensate droplets (a spray type contact condenser container). Alternatively, the condensate may be introduced back into and mixed with the gas stream in a form of a gravity flow down the interior sides of the exhaust line to be mixed with the gas stream (a drip type contact condenser container).

An internal cooling surface or device may be used to provide additional cooling to the interior of the contact condenser container. For example, in FIG. a tubing may be disposed within the contact condenser container to provide additional internal cooling. A cooling liquid or coolant may flow through the tubing. The internal cooling device also increase the turbulence within the moisture-containing gas stream as it passes through the contact condenser container to further promote the condensation of the moisture in the gas stream.

An external cooling surface or device may also be used to provide additional cooling to the contact condenser container. One or more external cooling surfaces may be positioned to come into contact with the external surface of the contact condenser container. A peristaltic pump or a pump with a disposable pump head may be used to provide a coolant flow for the additional external cooling to the contact condenser container. These external cooling surfaces may be cooled by thermoelectric Peltier modules. For example, a thermoelectric Peltier module (TE Technology, Inc., Traverse City, Mich.) may be used.

The advantages of the condensate recycling process disclosed herein may be even more significant when being used with a bioreactor having a high volume, for example, a volume greater than 50 Liters. As the volume of the bioreactor increases, the total gas flow rate increases and a large amount of moisture-containing gas stream is generated. Therefore, a system and method for high efficiency moisture condensation is desirable. Another scenario when the advantages are significant is related to the flow rate of the gas required per bioreactor volume. For example, a mammalian culture generally has a lower flow rate requirement per bioreactor volume regardless of the absolute size of the bioreactor than a low rate requirement for microbial cultures. A typical mammalian cell culture bioreactor run may require 0.1 Liters of gas flow rate per Liter of bioreactor volume. For typical microbial cultures this ratio is much higher. For example, a microbial culture may require 1.5 Liters of gas flow per Liter of bioreactor volume. Thus for reactions involving mammalian cell cultures, the condensate recycling would be useful in many cases especially as the bioreactor volume gets larger, while for reactions involving microbial cultures the condensate recycling would be useful in almost all cases regardless of the bioreactor size.

In FIG. 1, a contact condenser container 13 is fluidically coupled to a bioreactor 10 through an exhaust line 21. A condensate accumulator 16 is fluidically coupled to the contact condenser container 13 through at least a first condensate line 23 and a second condensate line 25; the condensate accumulator 16 is further fluidically coupled to the bioreactor 10 through at least a condensate overflow line 26. A condensate flow control device is used to direct and/or control the flow of the condensate. The condensate flow control device may comprise a pump, a check valve, a nozzle, or a pressurized air source, or a combination thereof. The exhaust line 21, the condensate lines (23 and 25), and the condensate overflow line 26 described herein may also be referred to as conduits, tubings, or flexible tubings.

A relatively hot moisture-containing gas steam leaving the bioreactor 10 exits from a headspace 11 of the bioreactor and enters the contact condenser container 13 via the exhaust line 21 in a flow direction of 110. The moisture in the gas stream is condensed inside the contact condenser container 13 to form a relatively cool condensate. A dry gas stream flows out of the contact condenser container 13 and enters a filter 18 via a fluid line 22.

In one embodiment, in the initial stage of the condensate recycling, after the relatively cool condensate is generated in the contact condenser container 13, it is released or drained into the first condensate line 23 and flows to a first pump 14 disposed on the first condensate line 23. The first pump 14 pumps the relatively cool condensate into the condensate accumulator 16. All or a portion of the relatively cool condensate may then be transferred back into and mixed with the relatively hot moisture-containing gas stream via the second condensate line 25. The release and flow of the cool condensate leaving the condensate accumulator 16 to be mixed with the gas stream may be directed and/or controlled by a second pump 15 disposed on the second condensate line 25. Pumps 14 and 15 may be the same or different. The flow rate of each pump can be set at a fixed speed, or a variable speed in which the speeds could be varied during the course of a bioreactor run either manually or under the control of a bioreactor control system.

The mixing of the cool condensate with the moisture-containing gas stream may occur in the exhaust line 21 by using a spray nozzle 12. The spray nozzle 12 is configured to produce and deliver a spray of cool condensate droplets into the gas stream. One or more spray nozzles may be used to spray the cool condensate back into the moisture-containing gas stream in the exhaust line 21. The nozzle spray pattern used for spraying the condensate could be one of those commonly used in other spray applications. Nozzle spray patterns that could be used with the contact condenser container may include, for example, Full Cone, Flat Fan or Mist/Fog. The nozzle(s) could have either a single orifice or could have multiple spray orifices built into the nozzle as is common in other spray applications.

Further in FIG. 1, the condensate accumulator 16 is fluidically coupled to the bioreactor 10 through at least the condensate overflow line 26. A condensate overflow control device, for example, a check valve 17, is disposed on the condensate overflow line 26; the check valve 17 is configured to direct the overflow of the cool condensate from the condensate accumulator 16 to the bioreactor 10.

The first pump 14 and the second pump 15 may operate at a fixed rate different from each other. The first pump may operate at a higher flowrate than the second pump. This difference in flowrates would cause a slow build-up of condensate and pressure in the condensate accumulator 16. At first when the condensate level in the condensate accumulator 16 is still below that of an overflow exit port (not shown), pressure will continue to increase until it reaches the cracking pressure of the check valve 17 and the check valve 17 will open. Air will now flow into the bioreactor through the condensate overflow line 26 until it has reduced the pressure in the condensate accumulator 16 to a point where the check valve 17 closes and the condensate leaving the contact condenser container 13 continues to flow into the condensate accumulator 16. At a later point the condensate collected will fill the condensate accumulator 16 to a level where the overflow exit port (not shown) is located. In this case when the pressure of the condensate accumulator 16 reaches the cracking pressure of the check valve 17, the check valve 17 opens, and some of the condensate in addition to the air will be forced to flow through the condensate overflow line 26 and into the bioreactor 10. From this point on the level of the cool condensate in the condensate accumulator 16 will not increase above an overflow mark (not shown) since some of the condensate will also flow into the bioreactor 10 whenever the check valve 17 opens but the flow rate of the overflow condensate from the condensate accumulator 16 to the bioreactor 10 can increase.

The check valves 17 disposed in the condensate overflow line 26 may be those commonly used in applications where a flow in one direction only is desired. Non-limiting examples of check valves include ball check valves (spring loaded or non-spring loaded) and diaphragm check valves. The check valves may be sterilized using sterilization methods that are commonly used to sterilize disposable, single use products. Examples of sterilization methods include, but are not limited to, gamma-irradiation, autoclaving (moist heat), ethylene oxide gas, chlorine dioxide gas, ozone gas, and vaporized hydrogen peroxide.

The check valve 17 would require a cracking pressure lower than the maximum operating pressure of the condensate accumulator 16 and associated tubings, but one that is higher than the maximum internal operating pressure inside the bioreactor 10.

A non-limiting example of maximum internal operating pressure of a disposable or single use bioreactor and a disposable or single use contact condenser container may be about 1.0 psi or less. The maximum operating pressure of a flexible silicone tubing such as one used in a single use system may be in the range of about 20 to 30 psi. A rigid condenser accumulator may have a maximum pressure of about 10 to 15 psi. A flexible condenser accumulator container such as a small bag may have a maximum pressure of about 5 psi.

Figure 2:
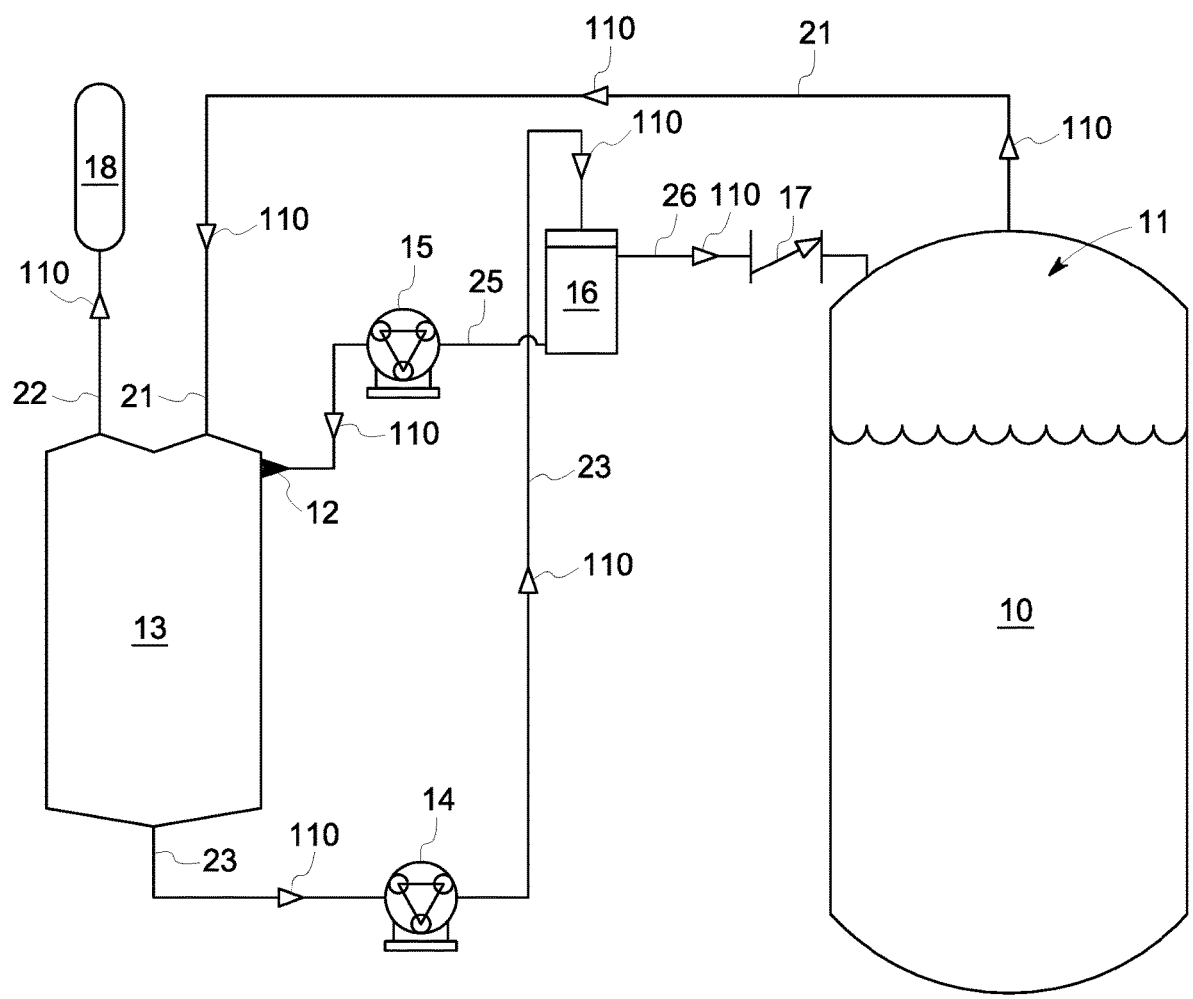
FIG. 2 is a schematic drawing of an example of a system according to an embodiment.

In FIG. 2, the recycled condensate is shown to be introduced back into and/or mixed with the moisture-containing gas stream inside the contact condenser container 13 rather than in the exhaust line 21.

The spray nozzle 12 may be positioned and configured such that the recycled condensate may be sprayed across the flow of the gas stream, with the flow of the gas stream or against the flow of the gas stream as the gas stream passes through the exhaust line 21 and into the contact condenser container 13.

Figure 3:
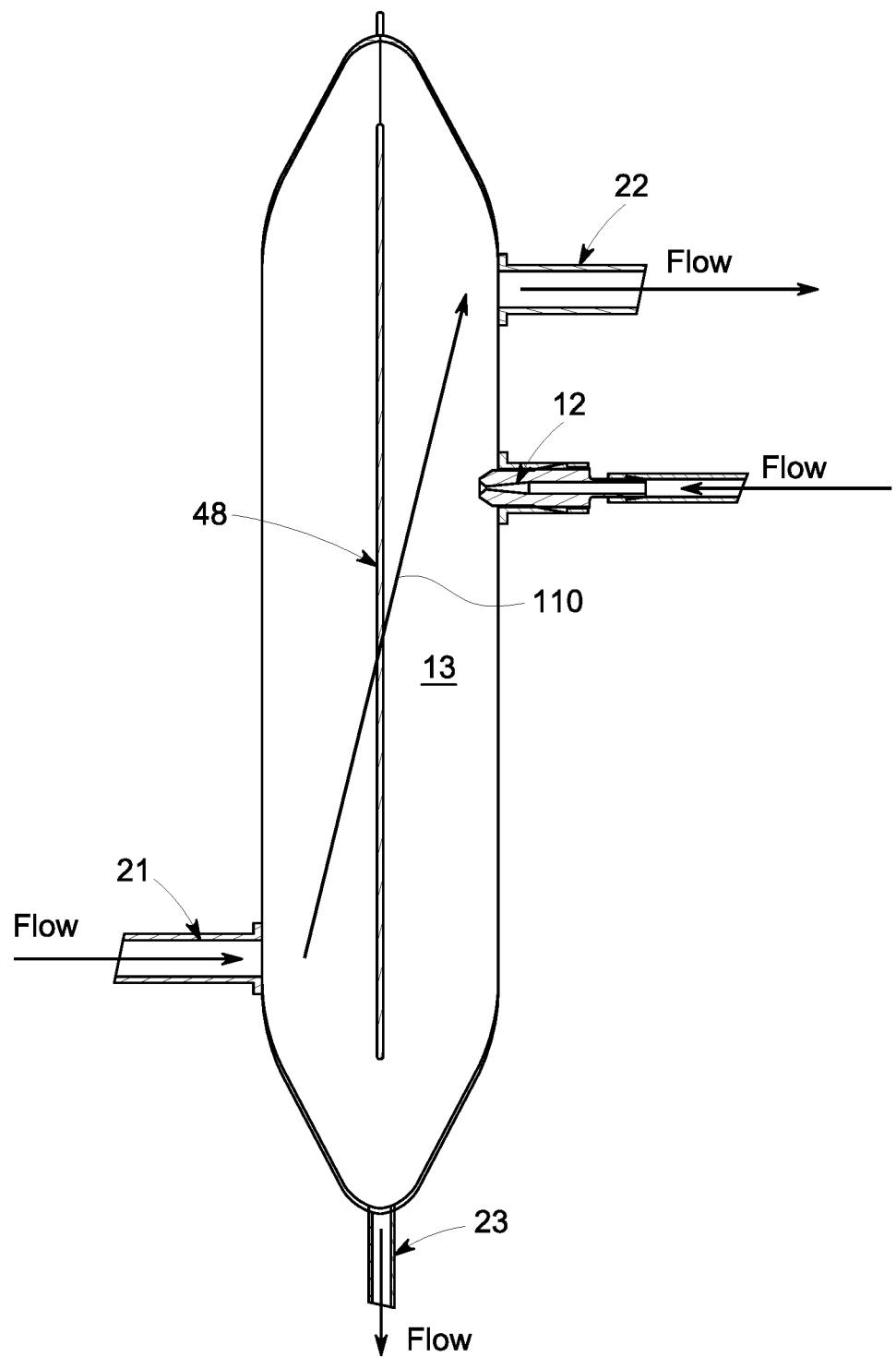
FIG. 3 is a cross sectional view of the example of a system according to an embodiment (partial view).

FIG. 3 is a partial cross sectional view of an example of a system according to an embodiment. Similar to the embodiment disclosed in FIG. 2, the spray nozzle 12 is attached directly to the contact condenser container 13 in FIG. 3. The recycled condensate is sprayed into the contact condenser container 13 with the spray nozzle 12, and is mixed with the moisture-containing gas stream as the gas stream passes through the contact condenser container 13.

An optional screen 48 may be disposed inside the contact condenser container 13 to provide additional turbulence to the gas stream and to provide a rough surface onto which droplets of the sprayed condensate can cling to. This increases the residence time of the recycled condensate in the gas stream to further increase cooling and mixing efficiency.

Figure 4:
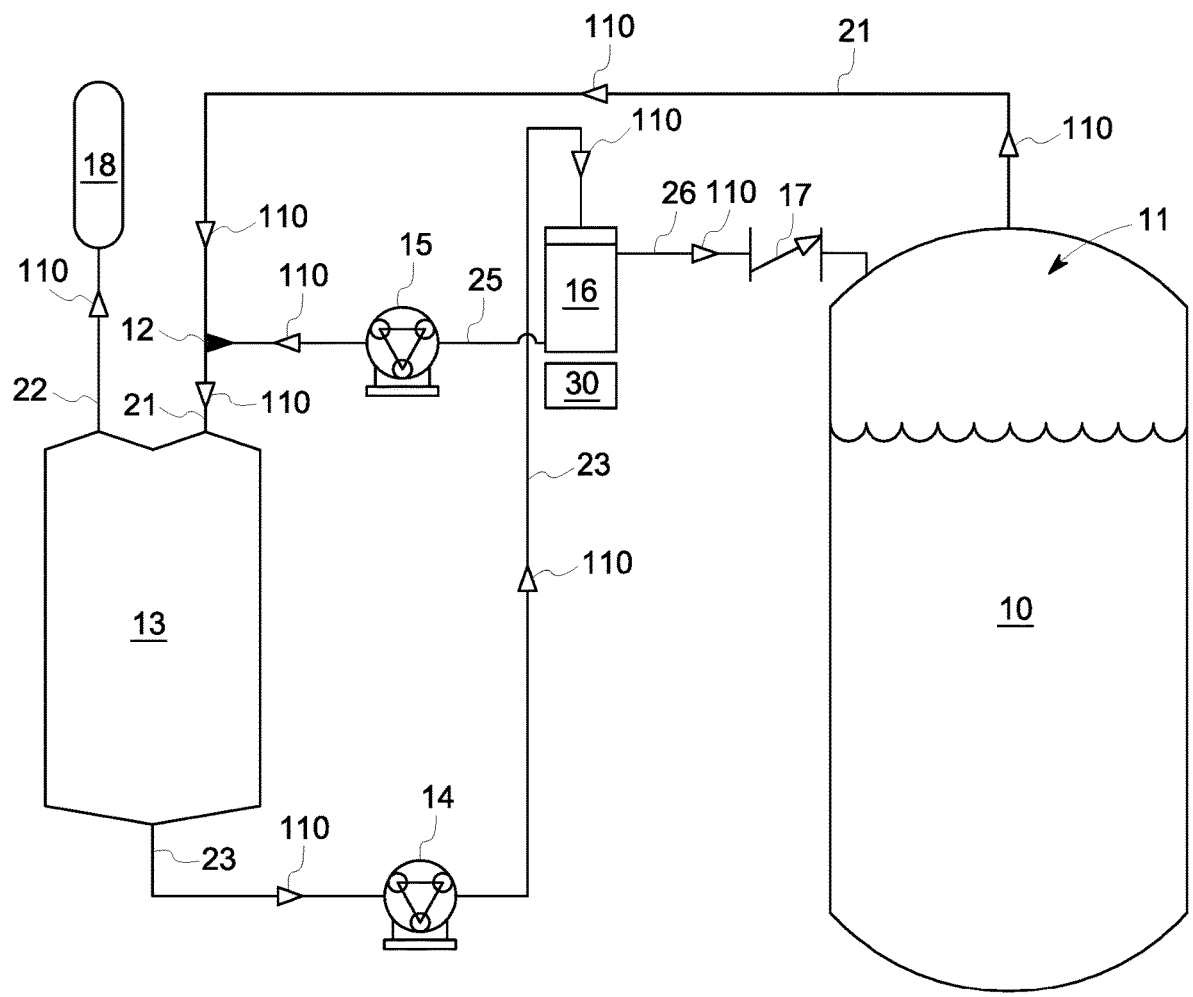
FIG. 4 is a schematic drawing of an example of a system according to an embodiment.

In FIG. 4, a cooler 30 is shown to provide cooling to the condensate accumulator 16 and to further cool the condensate inside the condensate accumulator 16 before the condensate is introduced back into and/or mixed with the moisture-containing gas stream. Further cooling the condensate increases the efficiency of the moisture condensation when the cooled condensate comes into contact with the containing gas stream. The cooler 30 shown in FIG. 4 may be applied to other embodiments.

The cooler 30 may be disposed externally to the condensate accumulator 16 and in direct contact with at least one outer surface of the condensate accumulator 16. For example, the cooler 30 may comprise a support structure (such as one or more plates or a container with an open top, not shown) with which the condensate accumulator 16 is placed in contact with. A cooling device such as a thermoelectric Peltier module may be attached to the walls of the support structure to provide the cooling.

Figure 5:
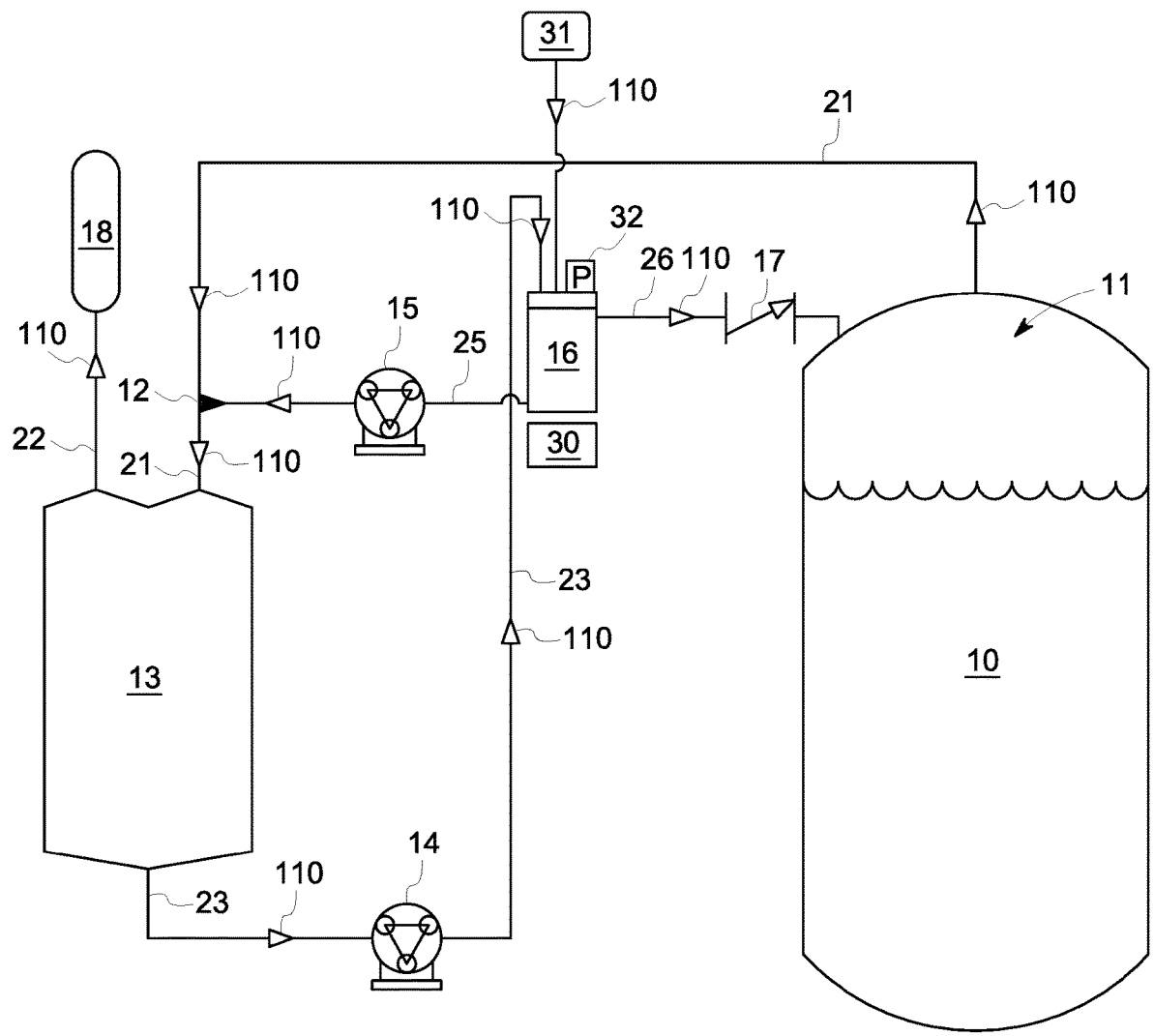
FIG. 5 is a schematic drawing of an example of a system according to an embodiment.

In FIG. 5, a pressurized air source 31 supplying pressurized air is fluidically coupled to the condensate accumulator 16. The additional pressure created by a flow of the pressurized air applied to the condensate accumulator 16 ensures that the pressure in the condensate accumulator 16 is sufficiently high to crack open the check valve 17 and force the condensate overflow to enter the bioreactor 10 against the pressure within the bioreactor 10. In some embodiments the pressurized air may be sterile.

A pressure sensor 32 may be coupled to the condensate accumulator 16 and used to monitor or provide a feedback for controlling the flow of the pressurized air to the condensate accumulator 16. The pressure sensor 32 may be further coupled to bioreactor system controller(s) (not shown) to allow the bioreactor system controller(s) to control the flow of the pressurized air to the condensate accumulator 16. Alternative pressure control mechanisms such as a low pressure gas regulator (not shown) may also be used with the pressure sensor 32 to control the flow of the pressurized air into the condensate accumulator 16.

In addition, the pressure sensor 32 may be used as a safety feature to ensure that the pressure inside the condensate accumulator 16 does not exceed the maximum operating pressure of the condensate accumulator 16. If the pressure inside the condensate accumulator reaches its maximum operating pressure as detected by the pressure sensor 32 then the flow of the pressurized air into the condensate accumulator 16 is stopped. The pressure sensor 32 shown in FIG. 5 may be applied to other embodiments.

Figure 6:
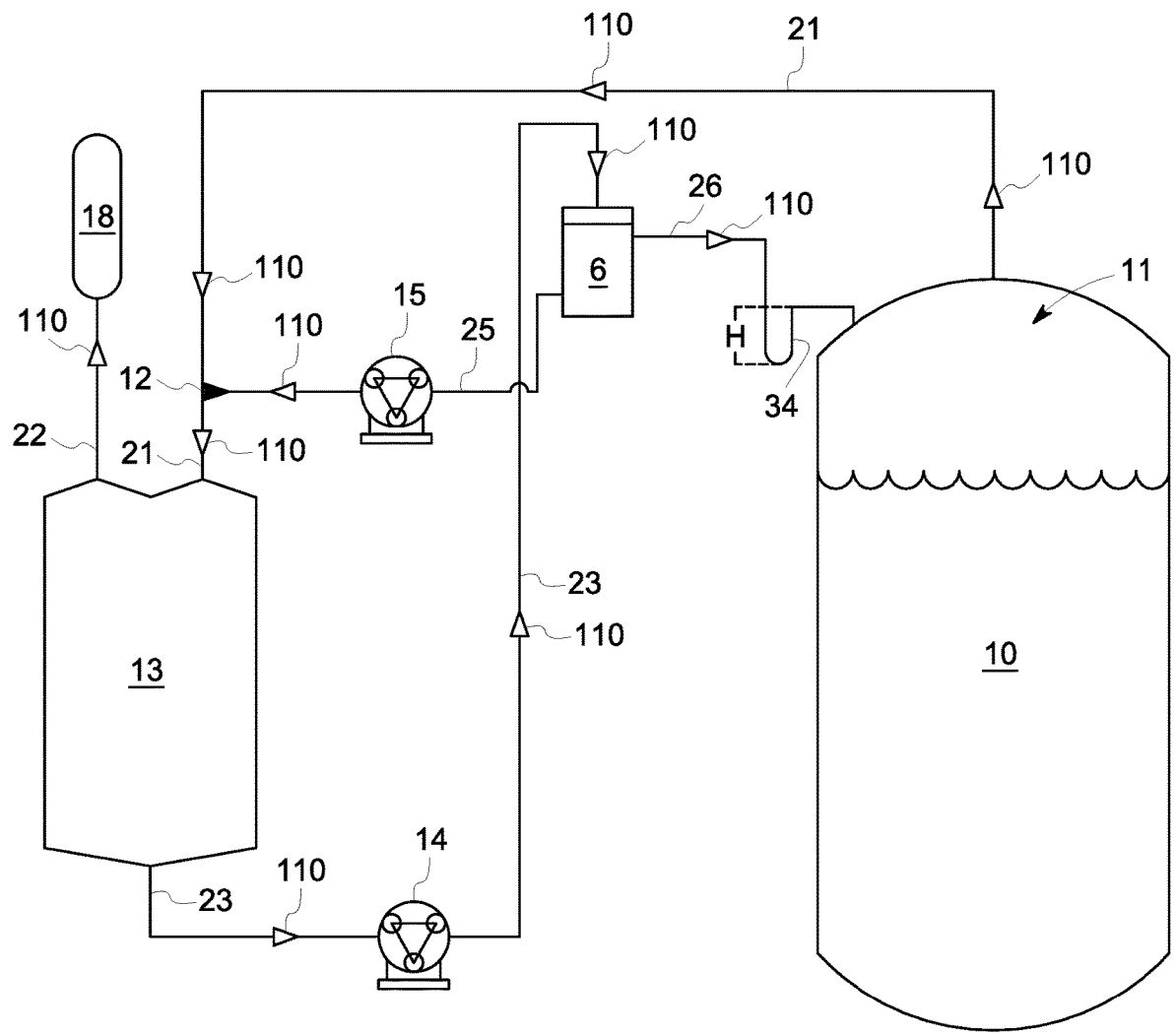
FIG. 6 is a schematic drawing of an example of a system according to an embodiment.

In FIG. 6, the condensate overflow line 26 comprises a length of tubing configured with a U-shaped bend and held in place through external clips (not shown) to form a trap 34. The trap 34 is configured to prevent backflow from the bioreactor 10 into the condensate accumulator 16 via the condensate overflow line 26. For example, the height (H) of the trap 34 may be configured to sufficiently overcome the maximum headspace pressure (P) of the bioreactor 10, where H (ft)/2.31>P (psig) with ft and psig denotes the unit for H and P, respectively. The pressure in the headspace 11 of the bioreactor 10 may be monitored by a bioreactor system controller (not shown). A non-limiting example of the maximum headspace pressure in a single use or disposable bioreactor may be about 1.0 psi or less, and a non-limiting example of the height of the trap 34 may be about 1.6 feet. When the condensate level in the condensate accumulator 16 reaches the overflow exit port (not shown), the condensate will fill the condensate overflow line 26 and gravity feed down to the trap 34 and into the bioreactor 10. Although a U-shaped bend is shown here as an example, one skilled in the art would appreciate that other forms and shapes could achieve the same purpose of preventing the backflow from the bioreactor 10 to the condensate accumulator 16. Traps with such other forms and shapes are intended to be included within the scope of the present invention.

Figure 7:
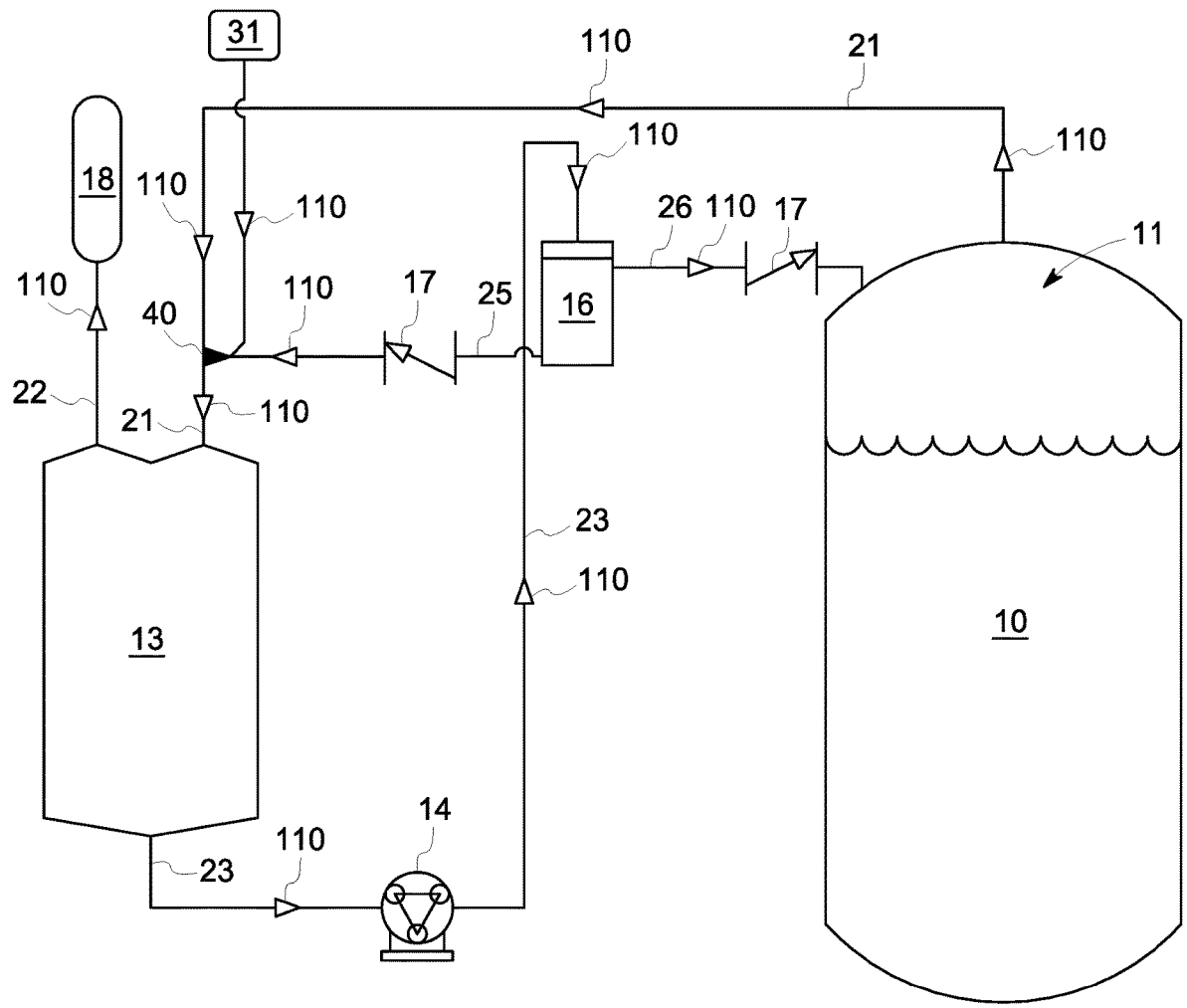
FIG. 7 is a schematic drawing of an example of a system according to an embodiment.

In FIG. 7, the pressurized air source 31 is coupled to a spray nozzle 40 to create a nozzle system such as a siphon fed nozzle system. A siphon fed nozzle system may use a flow of the pressurized air introduced into a stream of condensate in the nozzle 40 to create a pressure drop which would pull or draw the condensate from the condensate accumulator 16. The check valve 17 is shown coupling the spray nozzle 40 to the condensate accumulator 16. When the pressurized air source 31 is applied to the spray nozzle 40, the expansion of the pressurized air in the spray nozzle 40 creates a pressure drop which draws the recycled condensate through the check valve 17 from the condensate accumulator 16 to provide a fluid spray of the recycled condensate flowing from condensate accumulator 16.

In addition, the air pressure drop created as the stream of air exits from the nozzle provides additional cooling capacity to the recycled condensate as the pressurized air expands at the nozzle orifice and is sprayed into the moisture-containing gas stream.

In this embodiment, the condensate accumulator 16 is shown to be located above or at a level close to the level of the spray nozzle 12 so that the condensate is drawn into the spray nozzle 12 without the need to work against gravity. However, one of ordinary skill in the art would appreciate that the check valve 17 in this embodiment could be replaced with a pump to draw the condensate into the spray nozzle 12 against the gravity.

Figure 8:
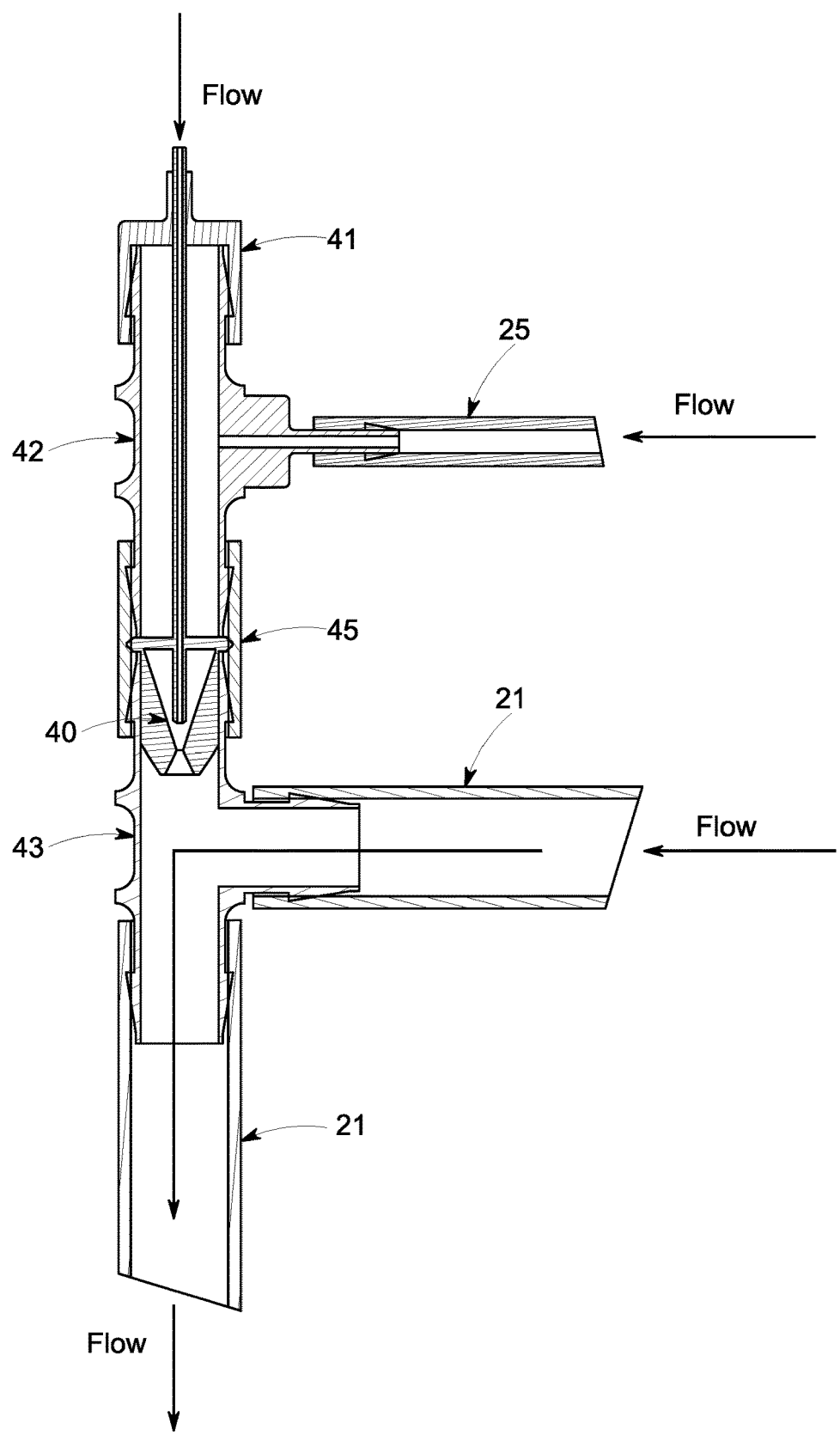
FIG. 8 is a cross sectional view of the example of FIG. 7 (partial view).
Figure 9:
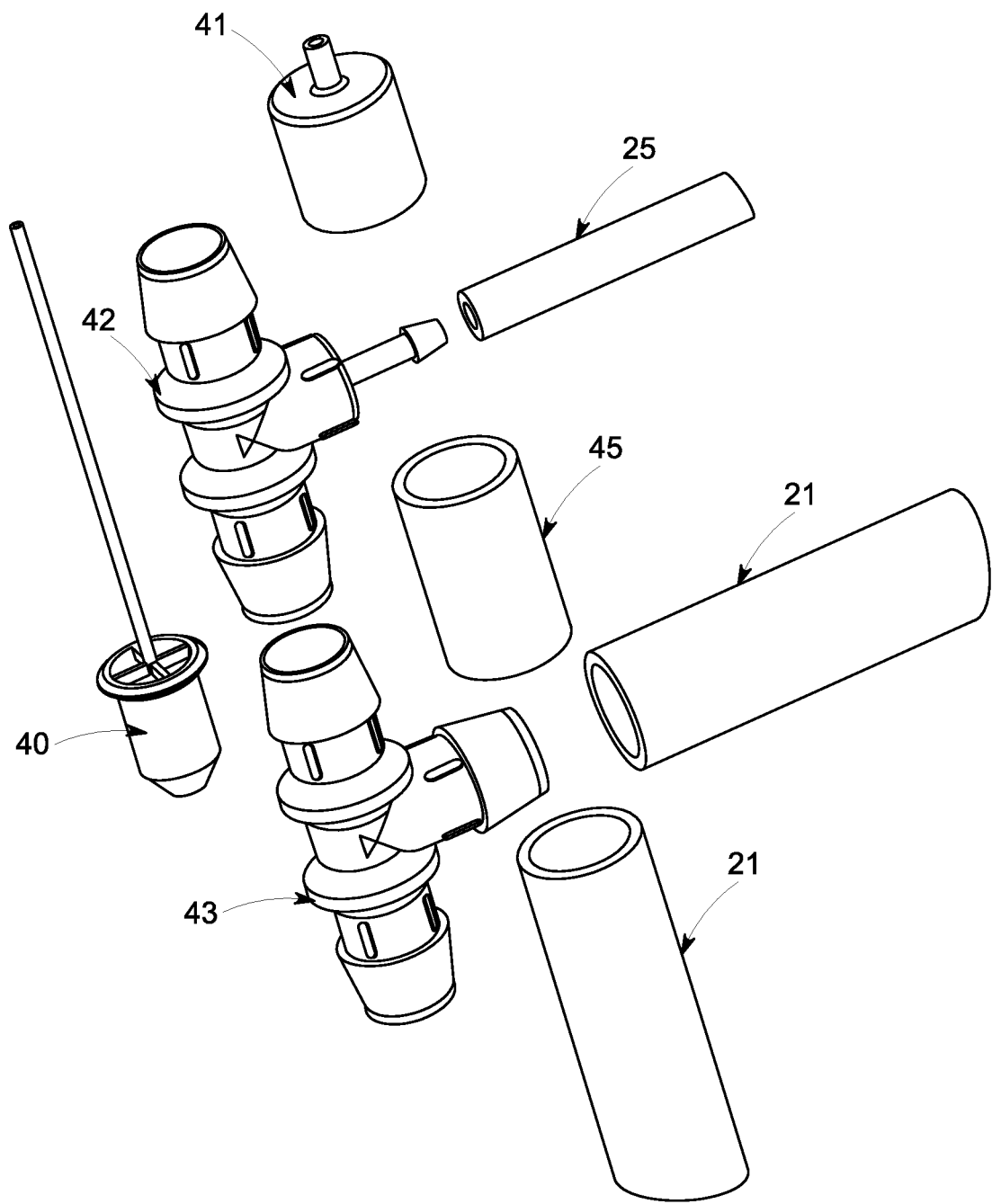
FIG. 9 is an exploded view of the example of FIG. 7 (partial view).

FIG. 8 and FIG. 9 show the partial cross-sectional view and the partial exploded view, respectively, of the example in FIG. 7. In FIG. 8, the flow direction of the recycled condensate entering the condensate line 25 is shown to be parallel to the flow direction of the moisture-containing gas stream entering the exhaust line 21 as an example, but other configurations of the flow directions are possible and are intended to be included within the scope of the present invention. For example, the flow direction of the recycled condensate may be across (perpendicular to) or parallel to but in opposition to the flow direction of the gas stream.

In FIG. 8 and FIG. 9, an embodiment of a siphon fed nozzle system assembled with commercially available parts is shown. The nozzle system comprises, for example, a siphon fed nozzle 40, an air feed sealing cap 41, a reduced barbed Tee Tube Fitting 42, and a barbed Tee Tube Fitting 43 (Nordson Medical, Loveland, Colo.). However, parts comprising one or more custom designed injection molded plastic parts may also be used.

Figure 10:
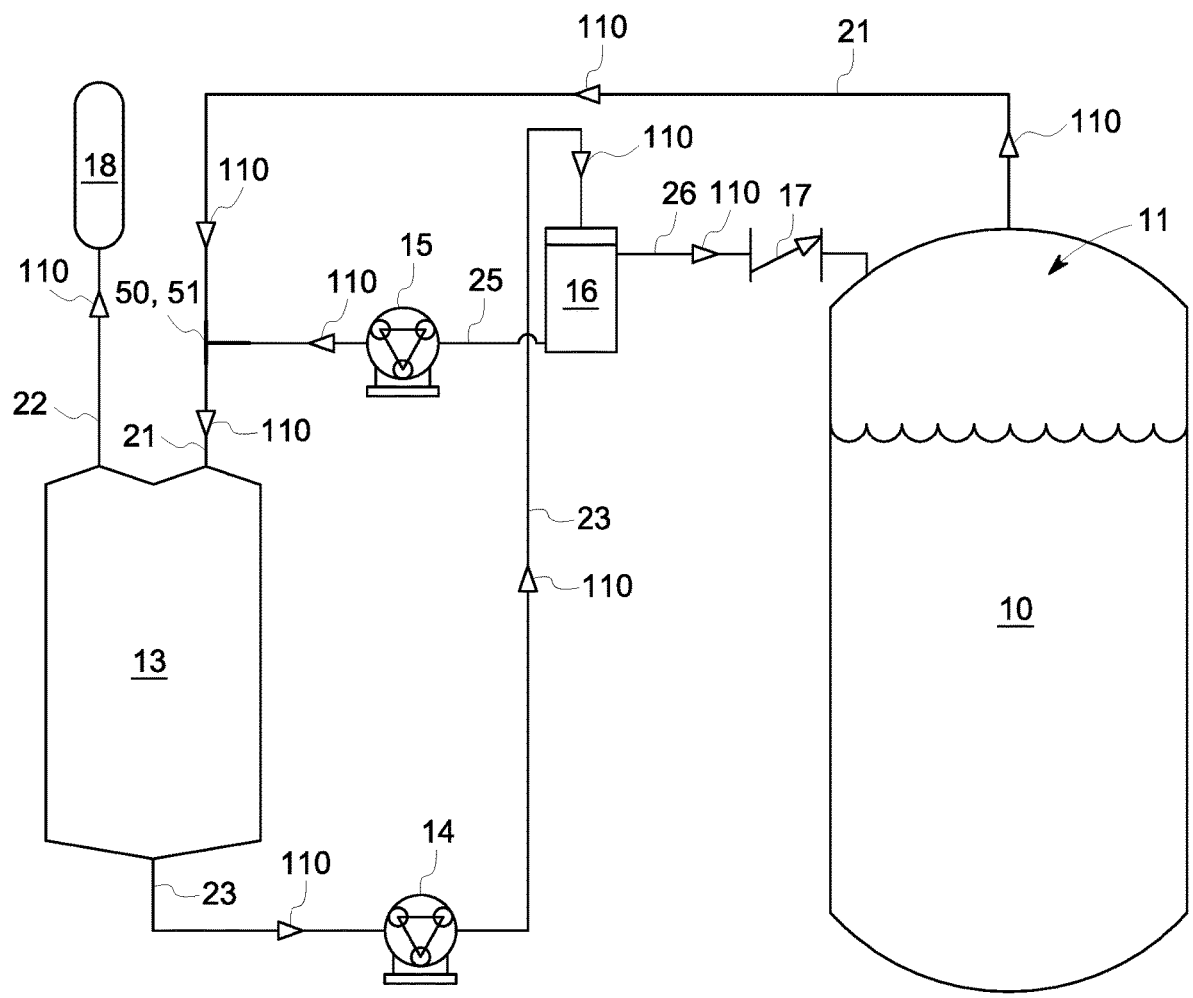
FIG. 10 is a schematic drawing of an example of a system according to an embodiment.

In FIG. 10, a recycled condensate from the condensate accumulator 16 is introduced back into the moisture-containing gas stream by using the second pump 15. However, instead of being sprayed into the gas stream, the recycled condensate is allowed to drip, or run down the interior sides of the exhaust line 21 by gravity.

Figure 11:
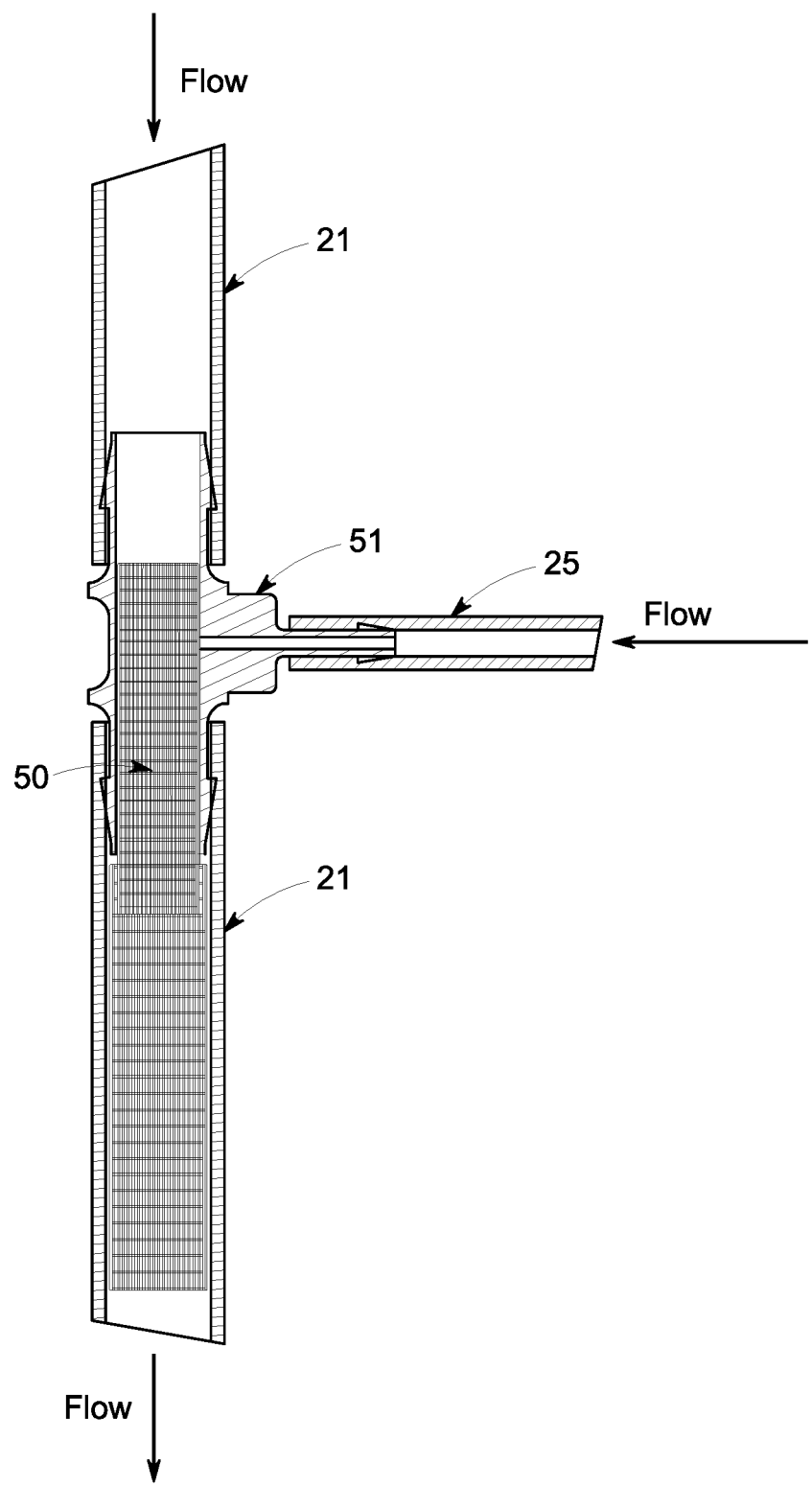
FIG. 11 is a cross sectional view of the example of FIG. 10 (partial view).
Figure 12:
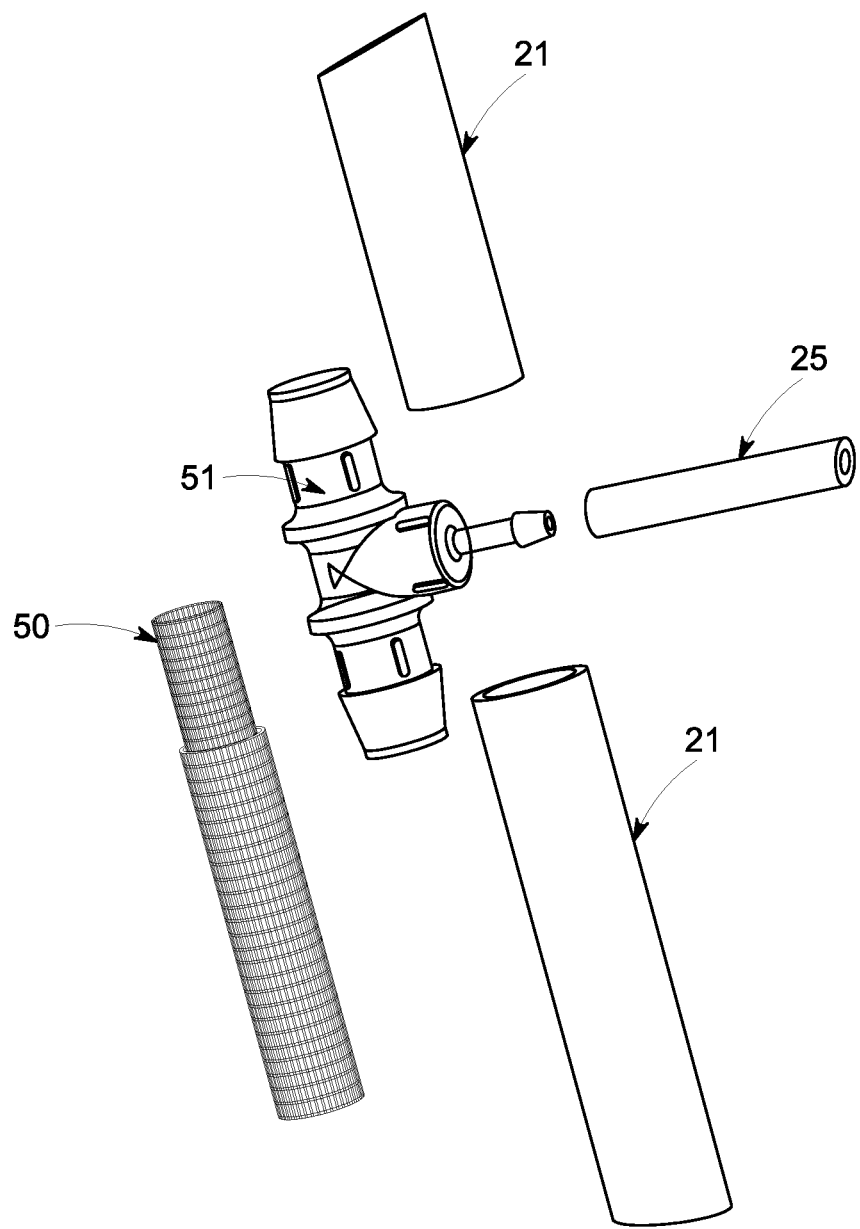
FIG. 12 is an exploded view of the example of FIG. 10 (partial view).

FIG. 11 and FIG. 12 show the partial cross-sectional view and the partial exploded view, respectively, of the example in FIG. 10. In FIG. 11, the flow direction of the recycled condensate entering the condensate line 25 is shown to be in a direction across (perpendicular to) the flow direction of the gas stream entering the exhaust line 21 as an example, but other configurations of the flow directions are possible and are intended to be included within the scope of the present invention. For example, the flow direction of the recycled condensate may be along (parallel to) the flow direction of the gas stream.

Optionally, at least one screen 50 may be disposed inside the interior of the exhaust line 21, with the screen 50 positioned to allow the flow of the recycled condensate leaving the condensate accumulator to pass over and collect on the screen(s). The condensate may also be allowed to simply run along the inside wall of the exhaust line 21. The optional screen 50 and a barbed Tee Tube Fitting 51 in FIG. 12 are shown here for illustration purpose only. Many other alternative configurations may be used in the present invention, including, for example, a screen wound into a tubular spiral, a screen folded into a lobed tubular shape, a screen folded into a pleated shape, a screen assembly as a series of stacked, circular discs, or a spiral, spring shaped coil.

Figure 13:
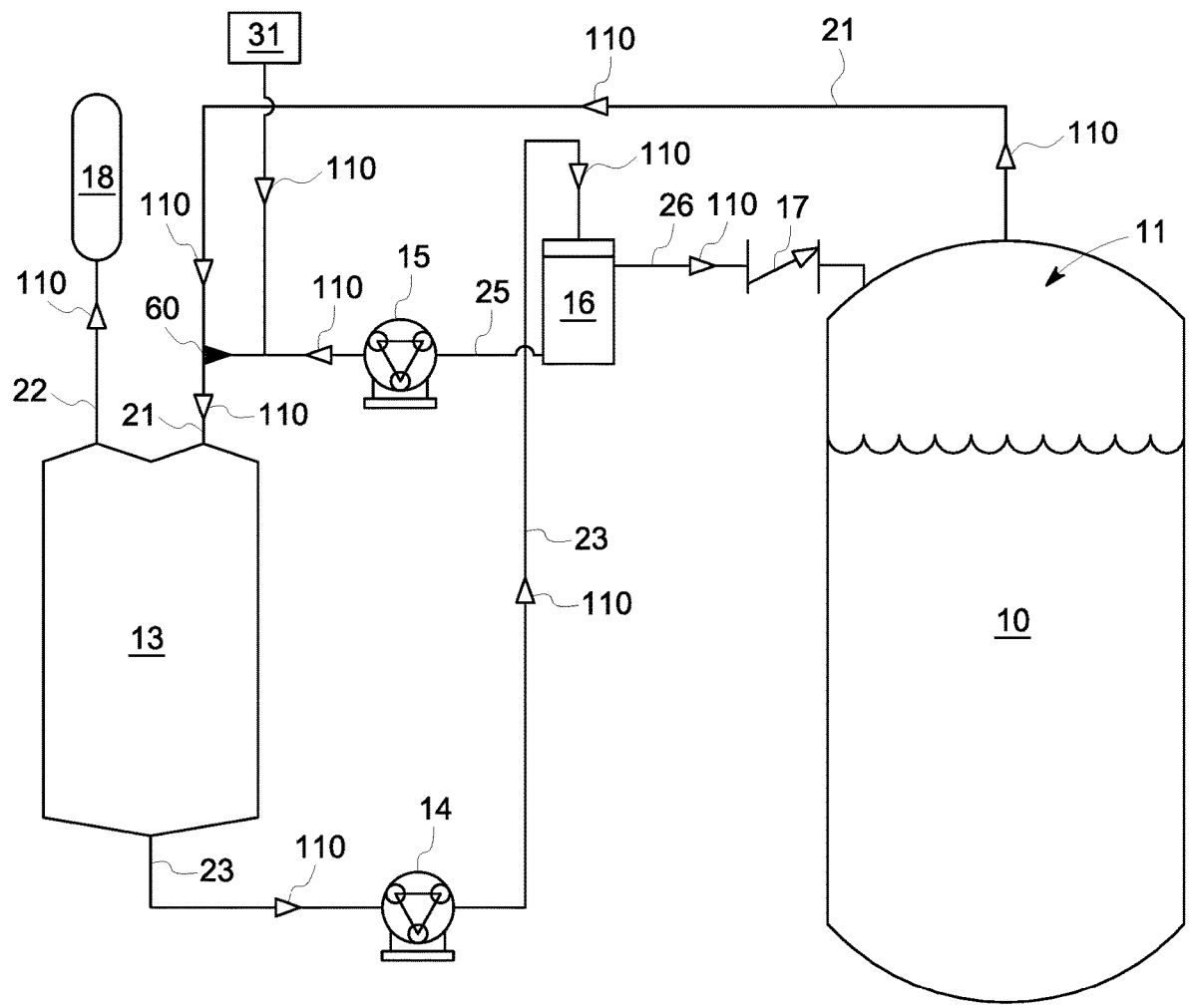
FIG. 13 is a schematic drawing of an example of a system according to an embodiment.

In FIG. 13, a pump fed nozzle system is shown. The pump 15, when used with or without the assistance of the pressurized air source 31, pushes or drives the recycled condensate through a spray nozzle 60 and produces a spray of the condensate in the moisture-containing gas stream. This configuration is different from the siphon fed nozzle system shown in FIG. 7, where the flow of pressurized air through the spray nozzle 40 draws the condensate into the spray nozzle 40.

During the early stages of a bioreactor run when not much condensate has been generated the expansion of the pressurized air in the spray nozzle will have some cooling effect on the flow of the air and will by itself assist to some extent in condensing the moisture from the gas stream.

Figure 14:
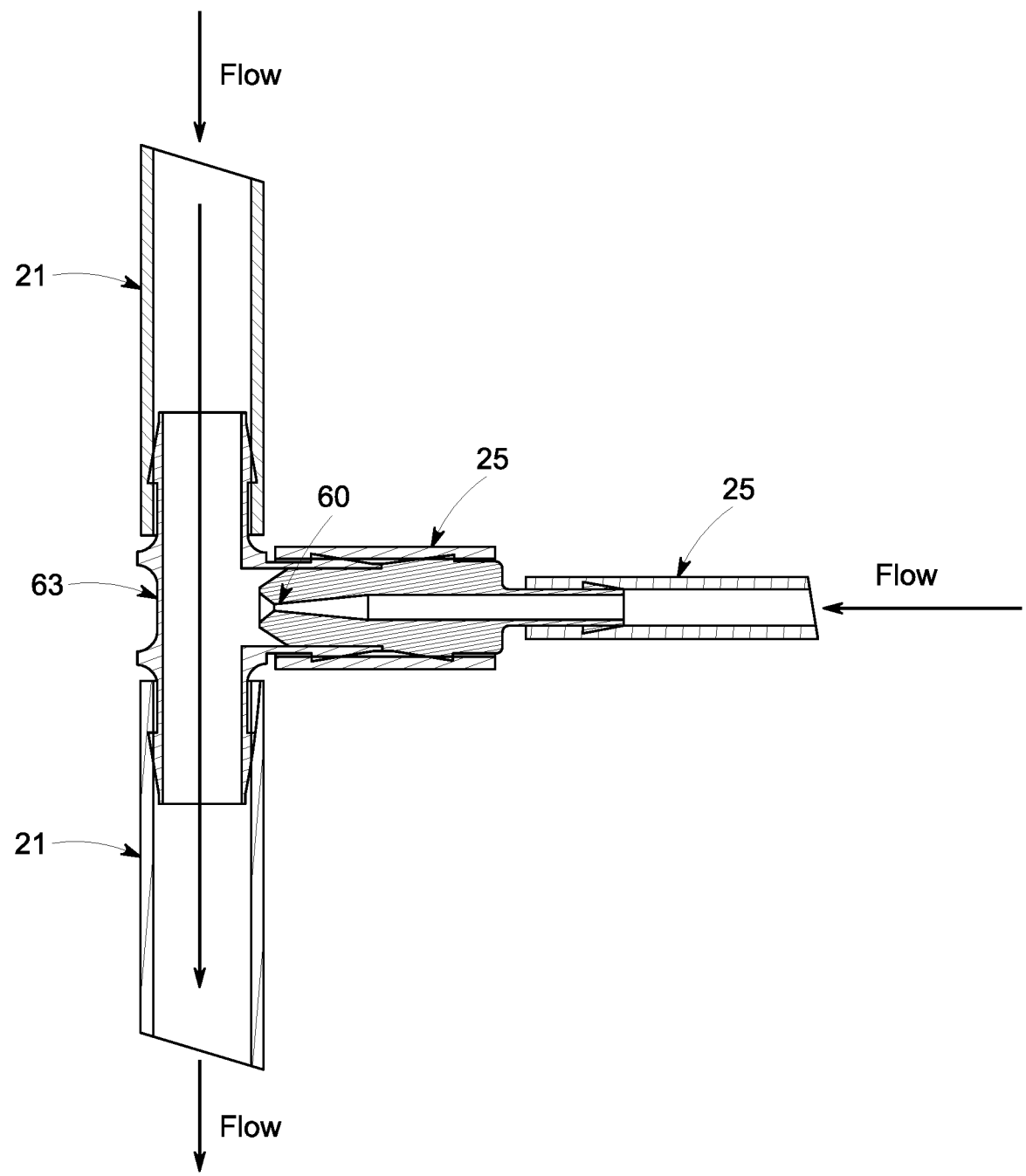
FIG. 14 is a cross sectional view of the example of FIG. 13 (partial view).
Figure 15:
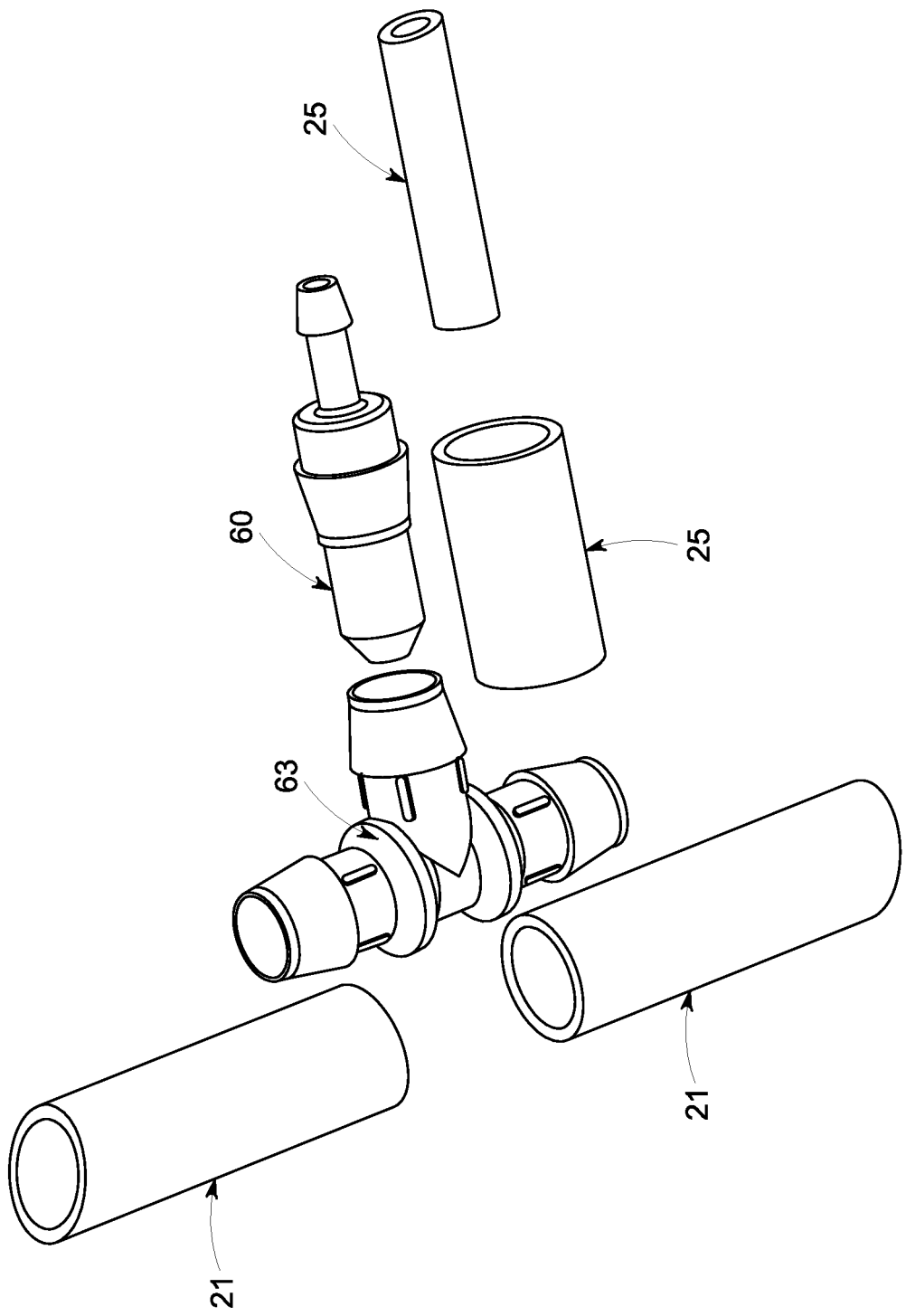
FIG. 15 is an exploded view of the example of FIG. 13 (partial view).
Figure 16:
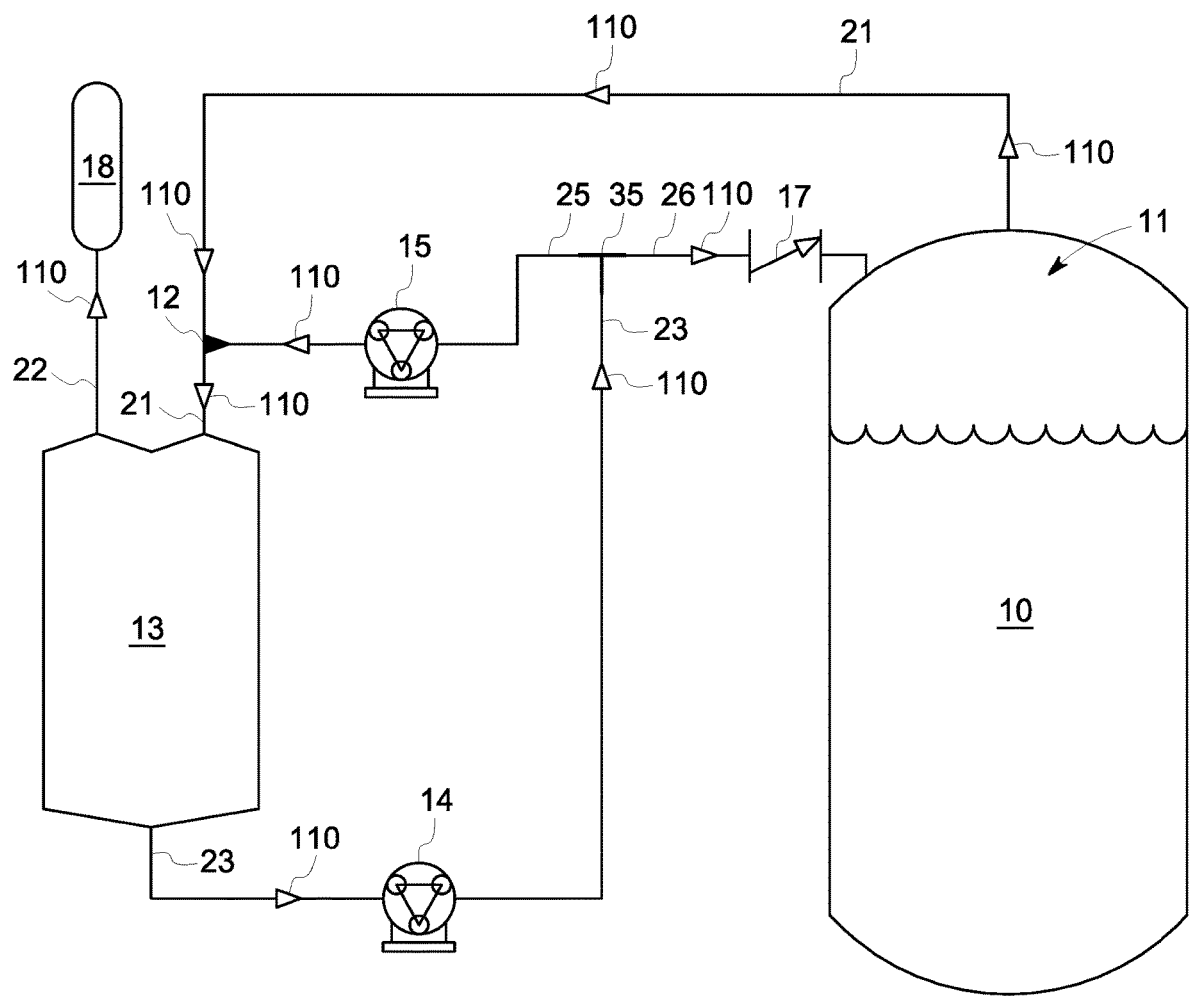
FIG. 16 is a schematic drawing of an example of a system according to an embodiment.
Figure 17:
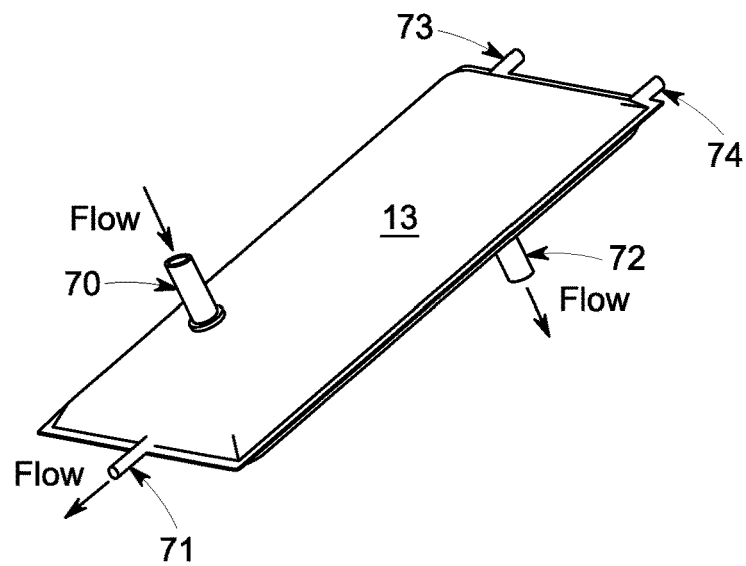
FIG. 17 is a perspective view of an example of a contact condenser container according to an embodiment.
Figure 18:
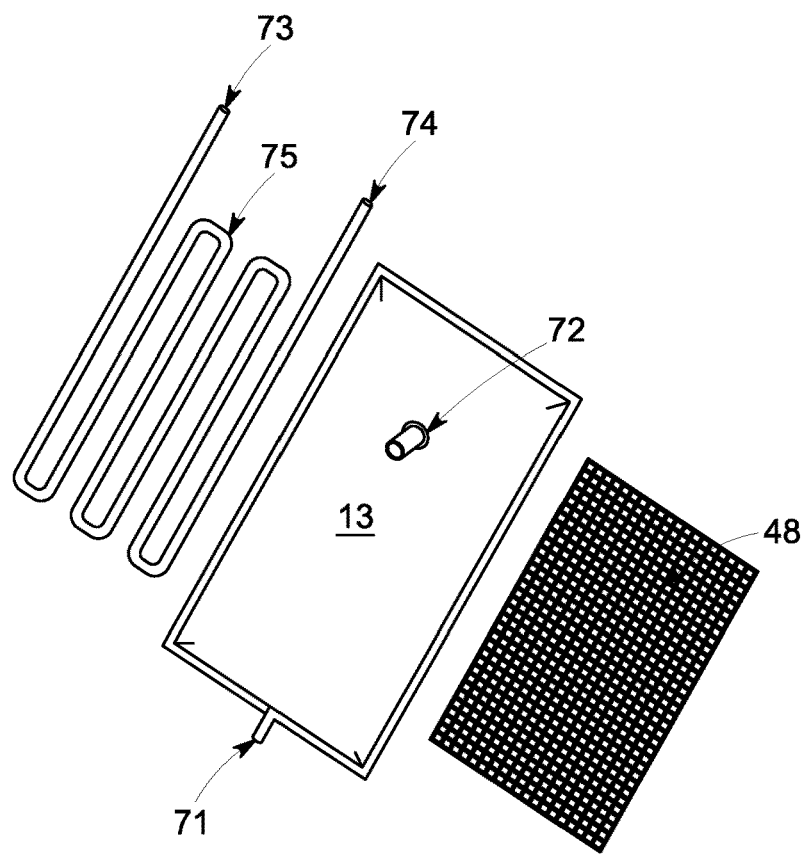
FIG. 18 is an exploded view of the example of FIG. 17.

FIG. 14 and FIG. 15 show the partial cross-sectional view and the partial exploded view, respectively, of the example in FIG. 13. In FIG. 14, the flow direction of the recycled condensate entering the condensate line 25 is shown to be in a direction across (perpendicular to) the flow direction of the gas stream entering the exhaust line 21 as an example, but other configurations of the flow directions are possible. For example, the flow direction of the recycled condensate may be along (parallel to) the flow direction of the gas stream or parallel to but in opposition to the flow direction of the gas stream.

In FIG. 14 and FIG. 15, an embodiment of the pump fed nozzle system assembled with commercially available parts is shown. The nozzle system comprises, for example, a barbed Tee Tube Fitting 63 (Nordson Medical, Loveland, Colo.). However, parts comprising one or more custom designed injection molded plastic parts may also be used.

In FIG. 16, the condensate accumulator is replaced with a tubing "Y" fitting or "T" fitting 35. In this embodiment, the first pump 14 operates at a higher speed than the second pump 15. The first pump 14 directs the condensate from the contact condenser container 13 to the fitting 35 in such a manner that the ratio of the flowrate of the second pump 15 to the first pump 14 correlates with the amount of condensate recycled back into the gas stream. The remaining condensate that is not recycled back into the gas stream is returned to the bioreactor 10 through the condensate overflow line 26. The condensate that is being pumped back into the gas stream may be pumped directly into the exhaust line 21 or through the spray nozzle 12 to form a spray of condensate droplets. The spray nozzle 12 may also be configured to be used with the pressurized air source 31 to assist disperse a small volume of the recycled condensate to form a spray of condensate droplets that may not be achieved by using the pumps alone.

FIG. 17 is a perspective view of a disposable contact condenser container 13. The contact condenser container 13 is shown to comprise an inlet port 70 and an outlet port 72 located on the outer wall of the contact condenser container 13 and allows a moisture-containing gas stream to enter and exit the contact condenser container 13, and a port 71 for the cool condensate to exit the contact condenser container 13. The contact condenser container 13 further comprises an internal cooling device 75 (an example of 75 is shown in FIG. 18) with two ending ports 73, 74 which may act as an inlet port or an outlet port to allow a coolant to flow through the internal cooling device 75 to provide additional cooling and promote the condensation of moisture in the gas stream passing through the contact condenser container 13.

FIG. 18 is an exploded view of a contact condenser container according to one embodiment. The internal cooling device 75 is disposed within the contact condenser container 13 to promote the condensation of moisture in the gas stream passing through the contact condenser container 13, and also serves to increase the turbulence within the gas stream as it passes through the contact condenser container 13.

In FIG. 18, the internal cooling device 75 is shown in a form of a length of a tubing and configured to have a serpentine shape such that it substantially completely fills the gap between the two inner layers of the contact condenser container 13. The contact condenser container assembly may further include at least one screen 48 disposed inside the contact condenser container 13, the screen 48 is configured to allow the condensate generated from the moisture-containing gas stream to be collected on the screen 48 before the condensate exits the contact condenser container 13. Allowing the condensate to be collected on and cling to the screen 48 increases the residence time of the condensate in the gas stream which increases the cooling and mixing efficiency of the contact condenser container 13.

Other internal cooling device structure may be arranged to allow condensation to form thereon, and/or to increase turbulence. Non-limiting examples include a series of fins attached to a support, and a spiral coil. The internal cooling device 75 may be flexible, rigid, or semi-rigid. Any structure within the contact condenser container 13 that can promote turbulence and/or promote moisture condensation is within the scope of the invention.

In addition, the contact condenser container 13 may be used in conjunction with an external cooling source to lower the temperature of a moisture-containing gas stream entering or leaving a bioreactor, further increasing the efficiency of the moisture condensation within the contact condenser container 13. In one embodiment, at least one surface of the contact condenser container 13 is in contact with an external cooling source, for example, at least one cold plate (not shown), which by conduction cools at least one surface, for example top surface of the contact condenser container 13, which in turn cools the inside surface of the contact condenser container 13 and cools the moisture-containing gas stream to or below its dew point temperature as the moisture-containing gas stream flows over the cooled surface.

In one embodiment, the at least one cold plate is appropriately sized to approximately match the surface area of one side of the contact condenser container 13 to maximize its contact area with the contact condenser container 13. The at least one cold plate may be attached to the cold side of a thermoelectric Peltier module.

In another embodiment, provision is made on the cold plate to provide a means of securing the contact condenser container 13 in position on the cold plate in order to ensure that at least one surface of the contact condenser container 13 is in contact with the cold plate surface.

In yet another embodiment, the least one cooling plate has a baffled pattern configured to direct a flow path within an interior chamber of the contact condenser container 13. The contact condenser container 13 may be sandwiched between two cooling plates.

Figure 19:
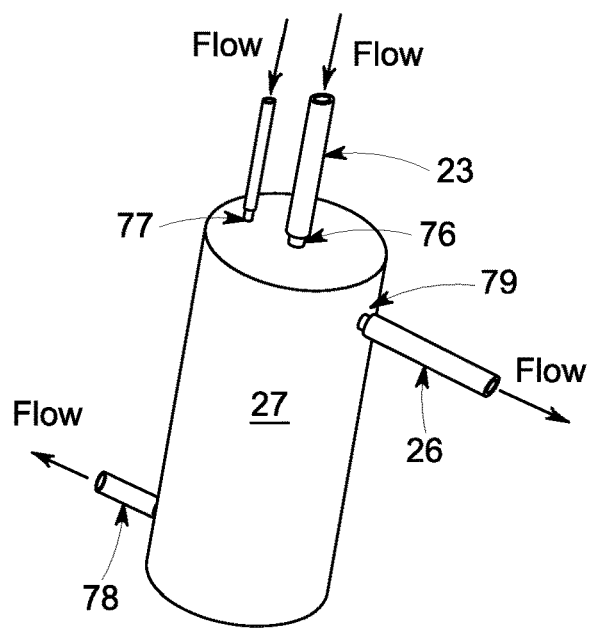
FIG. 19 is a perspective view of an example of a condenser accumulator according to an embodiment.

FIG. 19 is a perspective view of an example of a condenser accumulator according to one embodiment. In FIG. 19, a rigid condensate accumulator 27 has a first condensate port 76 through which a cool condensate leaving the contact condenser container 13 is added to the condensate accumulator 27. The condensate accumulator 27 also has an optional pressurized air flow port 77 through which a flow of sterile pressurized air may be applied to pressurize the condensate accumulator 27 if needed. Near the bottom of the condensate accumulator 27 is a second condensate port 78 that allows the condensate to flow out of the condensate accumulator 27 to the contact condenser container 13. A condensate overflow port 79 is located near the top of the condensate accumulator 27 and the location of the condensate overflow port 79 on the condensate accumulator 27 is higher than that of the second condensate port 78. The condensate overflow port 79 ensures that the level of condensate in the condensate accumulator 27 does not fill above a condensate overflow line (not shown) in the condensate accumulator 27.

Figure 20:
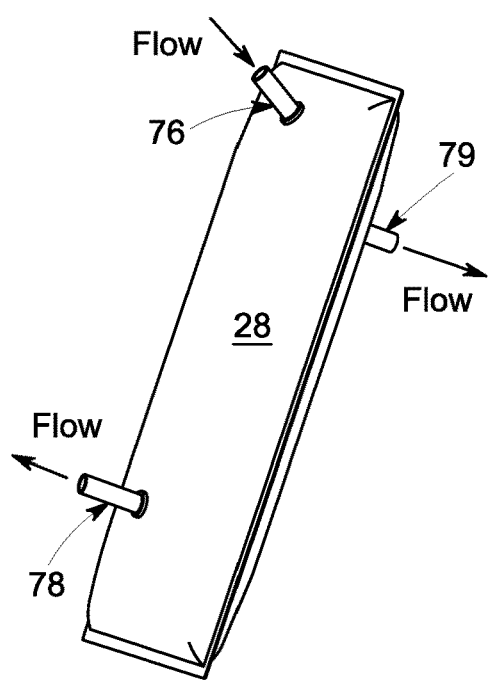
FIG. 20 is a perspective view of an example of a condenser accumulator according to an embodiment.

FIG. 20 shows one representative embodiment of a flexible condensate accumulator 28, with similar structural components as described for the rigid condensate accumulator 27. Also similar to the rigid condensate accumulator 27, the flexible condensate accumulator 28 may also comprise an optional pressurized air flow port (not shown) through which the sterile pressurized air may be applied to pressurize the condensate accumulator 28 if needed.

Figure 21:
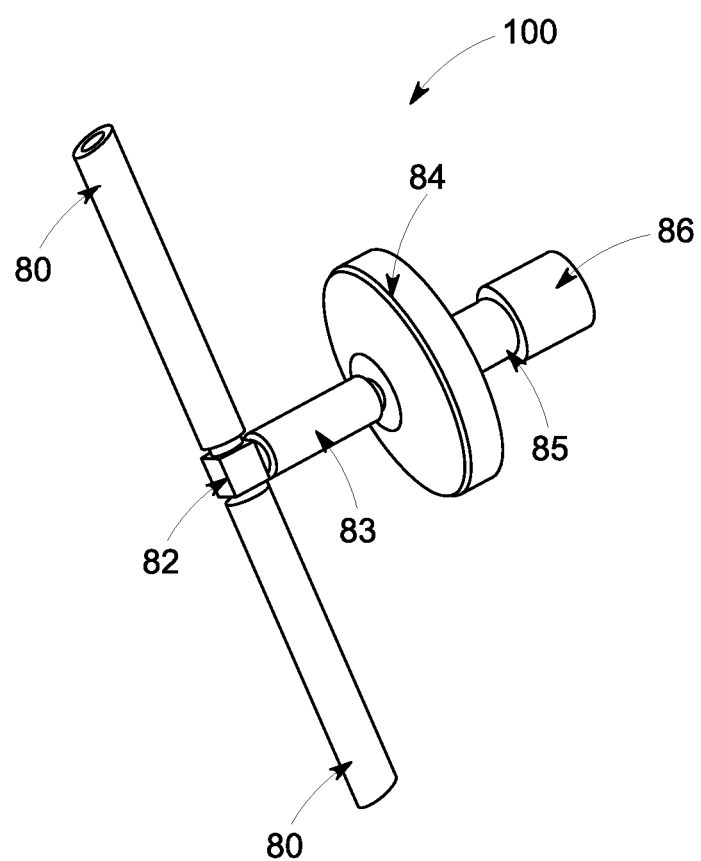
FIG. 21 is a perspective view of an example of a condensate priming system according to an embodiment.

FIG. 21 is a perspective view of an example of a condensate priming system according to an embodiment. The condensate priming system 100 may be part of a gas condensation system such as the one shown in FIG. 1. For example, the condensate primer 100 may be disposed anywhere in the condensate lines, for example, in the first condensate line 23 as shown in FIG. 1, between the contact condenser container 13 and the condensate accumulator 16, or in the second condensate line 25 between the condensate accumulator 16 and the contact condenser container 13. Other locations in the condensate flow path may also be used for disposing the condensate priming system 100.

The condensate priming system 100 comprises a priming fitting 82, a length of tubing 83, a sterile filter 84, a sterile connector 85, and a connector end cap 86. The sterile filter 84 keeps the condensate lines (for example, 80) sterile when priming with water and/or the cool condensate. The sterile connector 85 may be a Luer connector. However, other sterile connectors, for example, Pall Kleenpak connectors or Colder AseptiQuik sterile connectors, may also be used.

Figure 22:
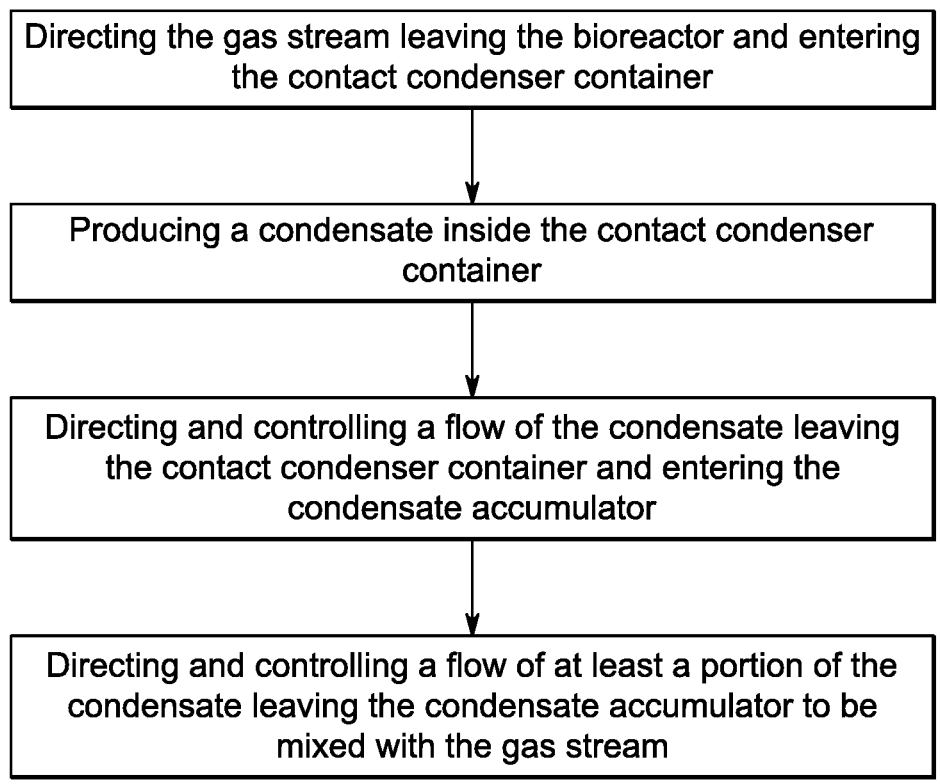
FIG. 22 is a schematic drawing of an example of a method according to an embodiment.

FIG. 22 is a schematic drawing of an example of a method of condensing moisture in a gas stream entering or leaving a bioreactor, according to an embodiment. The method includes the steps of: directing the gas stream leaving the bioreactor and entering the contact condenser container; producing a condensate inside the contact condenser container; directing and controlling a flow of the condensate leaving the contact condenser container and entering the condensate accumulator; and directing and controlling a flow of at least a portion of the condensate leaving the condensate accumulator to be mixed with the gas stream.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A system for condensing moisture in a gas stream of a bioreactor, the system comprising:
a contact condenser container fluidically coupled to a bioreactor through an exhaust line such that the exhaust line supplies a gas stream bearing condensate exiting the bioreactor to the contact condenser container;
a condensate accumulator fluidically coupled to the bioreactor through said exhaust line;
the condensate accumulator fluidically coupled to the contact condenser container through at least a first condensate line and a second condensate line;
the condensate accumulator further fluidically coupled to the bioreactor through a condensate overflow line;
wherein the second condensate line is directly connected to the exhaust line to supply condensate to the gas stream exiting the bioreactor before it enters the contact condenser container.

2. The system of claim 1 further comprising: wherein at a first condensate level condensate in the condensate accumulator is returned to the exhaust line via the second condensate line; and, at a second condensate level condensate is returned to the bioreactor through the condensate overflow line.

3. The system of claim 1 further comprising: wherein condensate is held in the condensate accumulator and released into the bioreactor in response to a volume of fluid in the bioreactor.

4. The system of claim 1 further comprising: wherein condensate held in the condensate accumulator is released to the exhaust line to increase the contact condenser container efficiency.

5. The system of claim 1 further comprising: wherein condensate is held in the condensate accumulator and released into the bioreactor in response to a change in nutrient concentration.

6. The system of claim 5 further comprising: wherein the change in nutrient concentration is measured as a function of at least one of: turbidity, electrical conductivity, dissolved oxygen, osmolality, and pH.

7. The system of claim 1 further comprising: wherein the condensate accumulator is primed with a sterile fluid.

8. The system of claim 7 further comprising: wherein the condensate accumulator is primed via a priming system containing at least one selected from the group of: a priming fitting, a sterile connector, and a sterile filter.

9. The system of claim 1 further comprising: wherein condensate returned to the exhaust line from the condensate accumulator is in droplet form.

10. The system of claim 9 further comprising: wherein the droplets returned to the exhaust line decrease a temperature of the exhaust gas from the bioreactor in the exhaust line.

11. The system of claim 1 further comprising: wherein condensate returned to the exhaust line from the condensate accumulator is returned as a gravity flow down interior sides of the exhaust line.

12. The system of claim 1 further comprising: wherein at least one of: the contact condenser container, the condensate accumulator, the exhaust line, the first condensate line, the second condensate line, the condensate overflow line, and a combination thereof is made of materials configured for sterilization before operation.

13. The system of claim 1 further comprising: wherein flow of condensate between at least one of: the contact condenser to the condensate accumulator, the condensate accumulator to the exhaust line, and, the condensate accumulator to the bioreactor is regulated with at least one control device.

14. The system of claim 13 further comprising: wherein the at least one control device is at least one of: a pneumatic pressure differential, a pump, and a check valve.

15. The system of claim 14 further comprising: wherein a first control device is a first pump, a second control device is a second pump, the first and second pumps operationally positioned on differing condensate lines.

16. The system of claim 15 further comprising: wherein the first and second pumps maintain differing flow rates of condensate through their respective differing condensate lines.

17. A method of controlling condensate comprising:
providing a bioreactor with an exhaust line;
fluidically coupling a contact condenser container to the bioreactor through the exhaust line such that the exhaust line supplies a gas stream bearing condensate exiting the bioreactor to the contact condenser container;
providing a condensate accumulator configured to accumulate condensate with at least a first and a second condensate line and an overflow line;
fluidically coupling the condensate accumulator to the contact condenser container through the first condensate line;
moving condensate from the contact condenser container to the condensate accumulator through the first condensate line;
fluidically coupling the second condensate line from the condensate accumulator to the exhaust line; and,
fluidically coupling the condensate accumulator to the bioreactor through the condensate overflow line;
wherein the second condensate line is directly connected to the exhaust line to supply accumulated condensate to the gas stream exiting the bioreactor before it enters the contact condenser container.

18. The method of claim 17 further comprising:
returning condensate from the condensate accumulator to the exhaust line via the second condensate line when the condensate is at a first level; and,
returning condensate from the condensate accumulator to the bioreactor via the overflow line when the condensate is at a second level.

19. The method of claim 17 further comprising:
cooling condensate in the exhaust line by releasing at least one of: condensate, and, a sterile fluid from the condensate accumulator into the exhaust line.

20. The method of claim 17 further comprising:
controlling a flow of condensate between at least one of: the contact condenser to the condensate accumulator, the condensate accumulator to the exhaust line, and, the condensate accumulator to the bioreactor by providing at least one control device.

* * * * *